US008876812B2

(12) United States Patent
Aramayo

(10) Patent No.: US 8,876,812 B2
(45) Date of Patent: Nov. 4, 2014

(54) SELF-LIMITING ELECTROSURGICAL RETURN ELECTRODE WITH PRESSURE SORE REDUCTION AND HEATING CAPABILITIES

(75) Inventor: Thomas F. Aramayo, Draper, UT (US)

(73) Assignee: Megadyne Medical Products, Inc., Draper, UT (US)

( * ) Notice: Subject to any disclaimer, the term of this patent is extended or adjusted under 35 U.S.C. 154(b) by 944 days.

(21) Appl. No.: 12/703,475

(22) Filed: Feb. 10, 2010

(65) Prior Publication Data

US 2010/0217260 A1 Aug. 26, 2010

Related U.S. Application Data

(60) Provisional application No. 61/155,687, filed on Feb. 26, 2009.

(51) Int. Cl.
*A61B 18/16* (2006.01)

(52) U.S. Cl.
CPC ........... *A61B 18/16* (2013.01); *A61B 2018/167* (2013.01)
USPC .................... 606/32; 606/33; 606/34; 606/35; 606/41

(58) Field of Classification Search
CPC ...... A61B 18/04; A61B 18/08; A61B 18/082; A61B 18/12; A61B 18/14; A61B 18/16; A61B 2018/167; A61B 2018/1246; A61B 2018/1253; A61B 2018/1266
USPC .......................................... 606/32, 34, 35, 41
See application file for complete search history.

(56) References Cited

U.S. PATENT DOCUMENTS

| 3,089,496 A | 5/1963 | Degelman |
| 3,543,760 A | 12/1970 | Bolduc |
| 3,601,126 A | 8/1971 | Estes |
| 3,720,209 A | 3/1973 | Bolduc |
| 3,848,600 A | 11/1974 | Patrick, Jr. et al. |
| 4,088,133 A | 5/1978 | Twentier |
| 4,092,985 A | 6/1978 | Kaufman |

(Continued)

FOREIGN PATENT DOCUMENTS

| GB | 1 480 736 | 7/1977 |
| GB | 2 052 269 | 1/1981 |

(Continued)

OTHER PUBLICATIONS

Wald, et al., "Accidental Burns Associated With Electrocautery," JAMA, Aug. 16, 1971, vol. 217, No. 7, pp. 916-921.

*Primary Examiner* — Michael Peffley
*Assistant Examiner* — Khadijeh Vahdat
(74) *Attorney, Agent, or Firm* — Workman Nydegger

(57) ABSTRACT

A self-limiting electrosurgical electrode for use with electrosurgery and various other surgical procedures is disclosed. The electrode includes a heating element for generating heat to warm a patient resting upon the electrode. The electrode can also include one or more pads to prevent the creation of pressure sores or decubitus ulcers on a patient resting upon the electrode. The electrode has an effective bulk impedance equal to or greater than about 4,000 Ω·cm, which arises from resistive components, capacitive components, inductive components, or combinations thereof. Through the selection of the impedance characteristics for the electrode materials, and through tailoring of electrode geometries, the electrode of the present invention is self-regulating and self-limiting as to current density and temperature rise so as to prevent patient trauma.

25 Claims, 11 Drawing Sheets

(56) References Cited

U.S. PATENT DOCUMENTS

| | | | |
|---|---|---|---|
| 4,094,320 A | 6/1978 | Newton et al. | |
| 4,117,846 A | 10/1978 | Williams | |
| 4,166,465 A | 9/1979 | Esty et al. | |
| 4,188,927 A | 2/1980 | Harris | |
| 4,200,104 A | 4/1980 | Harris | |
| 4,207,904 A | 6/1980 | Greene | |
| 4,226,247 A | 10/1980 | Hauser et al. | |
| 4,231,372 A | 11/1980 | Newton | |
| 4,237,886 A | 12/1980 | Sakurada et al. | |
| 4,237,887 A | 12/1980 | Gonser | |
| 4,267,840 A | 5/1981 | Lazar et al. | |
| 4,304,235 A | 12/1981 | Kaufman | |
| 4,384,582 A | 5/1983 | Watt | |
| 4,387,714 A | 6/1983 | Geddes et al. | |
| 4,669,468 A | 6/1987 | Cartmell et al. | |
| 4,770,173 A | 9/1988 | Feucht et al. | |
| 4,799,480 A | 1/1989 | Abraham et al. | |
| 5,352,315 A | 10/1994 | Carrier et al. | |
| 5,354,790 A | 10/1994 | Keusch et al. | |
| 5,520,683 A | 5/1996 | Subramaniam et al. | |
| 5,830,212 A | 11/1998 | Cartmell et al. | |
| 5,836,942 A | 11/1998 | Netherly et al. | |
| 6,049,927 A * | 4/2000 | Thomas et al. | 5/632 |
| 6,053,910 A | 4/2000 | Fleenor | |
| 6,083,221 A | 7/2000 | Fleenor et al. | |
| 6,111,233 A | 8/2000 | Rock et al. | |
| 6,160,246 A | 12/2000 | Rock et al. | |
| 6,214,000 B1 | 4/2001 | Fleenor et al. | |
| 6,389,681 B1 | 5/2002 | Rock et al. | |
| 6,454,764 B1 | 9/2002 | Fleenor et al. | |
| 6,544,258 B2 | 4/2003 | Fleenor et al. | |
| 6,547,786 B1 | 4/2003 | Goble | |
| 6,548,789 B1 | 4/2003 | Rock et al. | |
| 6,582,424 B2 | 6/2003 | Fleenor et al. | |
| 6,666,859 B1 | 12/2003 | Fleenor et al. | |
| 6,713,733 B2 | 3/2004 | Kochman et al. | |
| 6,723,967 B2 | 4/2004 | Rock et al. | |
| 6,814,889 B1 | 11/2004 | O'Grady et al. | |
| 6,852,956 B2 | 2/2005 | Rock et al. | |
| 6,875,963 B2 | 4/2005 | Rock et al. | |
| 6,963,055 B2 | 11/2005 | Rock et al. | |
| 7,038,177 B2 | 5/2006 | Rock | |
| 7,166,102 B2 | 1/2007 | Fleenor et al. | |
| 7,202,443 B2 | 4/2007 | Rock et al. | |
| 7,367,971 B2 | 5/2008 | Fleenor et al. | |
| 2005/0101947 A1 | 5/2005 | Jarrard et al. | |
| 2008/0249521 A1 | 10/2008 | Dunning et al. | |
| 2008/0249524 A1 * | 10/2008 | Dunning | 606/41 |

FOREIGN PATENT DOCUMENTS

| | | |
|---|---|---|
| JP | S55-168317 | 12/1980 |
| JP | S57-154409 | 9/1982 |
| JP | S57-188250 | 11/1982 |
| JP | S63-54148 | 3/1998 |
| WO | WO 2008/013459 | 1/2008 |

* cited by examiner

SELF-LIMITING ELECTROSURGICAL RETURN ELECTRODE WITH PRESSURE SORE REDUCTION AND HEATING CAPABILITIES

CROSS-REFERENCE TO RELATED APPLICATIONS

This application claims priority to and the benefit of U.S. Provisional Patent Application Ser. No. 61/155,687, filed Feb. 26, 2009, entitled "SELF-LIMITING ELECTROSURGICAL RETURN ELECTRODE WITH HEATING CAPABILITIES," the disclosure of which is incorporated herein by this reference.

BACKGROUND

1. Technical Field

The present invention relates generally to electrosurgical systems. In particular, the present invention relates to electrosurgical return electrodes that are adapted to increase the comfort level of a patient positioned thereon. More specifically, the present invention relates to electrosurgical return electrodes that include both pressure sore reduction and heating capabilities.

2. The Relevant Technology

In the area of electrosurgery, medical procedures of cutting tissue and/or cauterizing leaking blood vessels are performed by utilizing radio frequency (RF) electrical energy. As is known to those skilled in the medical arts, electrosurgery is widely used and offers many advantages including that of the use of a single surgical tool for both cutting and coagulation. The RF energy is produced by a wave generator and transmitted to a patient's tissue through a hand-held electrode that is operated by a surgeon. For historical perspective and details of such techniques, reference is made to U.S. Pat. No. 4,936,842, issued to D'Amelio et al., and entitled "Electrosurgical Probe Apparatus," the disclosure of which is incorporated by this reference.

Every monopolar electrosurgical generator system must have an active electrode that is applied by the surgeon to the patient at the surgical site to perform surgery and a return path from the patient back to the generator. The active electrode at the point of contact with the patient must be small in size to produce a high current density in order to produce a surgical effect of cutting or coagulating tissue. The return electrode, which carries the same current as the active electrode, must be large enough in effective surface area at the point of communication with the patient such that a low density current flows from the patient to the return electrode. If a relatively high current density is produced at the return electrode, the temperature of the patient's skin and tissue will rise in this area and can result in an undesirable patient burn. According to the Emergency Care Research Institute, a well-known medical testing agency, the heating of body tissue to the threshold of necrosis occurs when the current density exceeds 100 milliamperes per square centimeter. Furthermore, the Association for the Advancement of Medical Instrumentation ("AAMI") has published standards that require that the maximum patient surface tissue temperature adjacent an electrosurgical return electrode shall not rise more than six degrees) (6°) Celsius under stated test conditions.

Over the past thirty years, industry has developed products in response to the medical need for a safer return electrode in two major ways. First, they went from a small, about 12×7 inches, flat stainless steel plate coated with a conductive gel placed under the patient's buttocks, thigh, shoulders, or any location where gravity can ensure adequate contact area to a flexible electrode. These flexible electrodes, which are generally about the same size as the stainless steel plates, are coated with a conductive or dielectric polymer and have an adhesive border on them so they will remain attached to the patient without the aid of gravity. Upon completion of the electrosurgical procedure, these flat flexible electrodes are disposed of By the early 1980's, most hospitals in the United States had switched over to using this type of return electrode. These return electrodes are an improvement over the old steel plates and resulted in fewer patient return electrode burns but have resulted in additional surgical costs in the United States of several tens of millions of dollars each year. Even with this improvement, hospitals were still experiencing some patient burns caused by electrodes that would accidentally fall off or partially separate from the patient during surgery.

Subsequently, there was proposed a further improvement, an Electrode Contact Quality Monitoring System that would monitor the contact area of the electrode that is in contact with the patient and turn off the electrosurgical generator whenever there was insufficient contact area. Such circuits are shown, for example, in U.S. Pat. No. 4,231,372, issued to Newton, and entitled "Safety Monitoring Circuit for Electrosurgical Unit," the disclosure of which is incorporated by this reference. This system has resulted in additional reduction in patient return electrode burns, but requires a special disposable electrode and an added circuit in the generator that drives the cost per procedure even higher. Twenty years after this system was first introduced, fewer than 40 percent of all the surgical operations performed in the United States used this system because of its high costs.

Although various advances have been made in the electrosurgical arts, there remains room for improvement. More particularly, while systems and devices have been developed to increase the safety of patients undergoing electrosurgical procedures, such as by reducing the number of patient return electrode burns, the comfort of these patients before, during, and after electrosurgical procedures remains lacking.

One cause of patient discomfort is the relatively low temperatures maintained in hospitals and particularly in operating rooms where electrosurgical procedures take place. Operating room temperatures are typically maintained between about 18.5-21° C. (65.3-69.8° F.). For many patients, this temperature range feels too cold. Additionally, during a surgical procedure patients may contact objects that have physical properties that cause the objects to feels even colder than they really are. For example, metal operating room tables and return electrodes may be good thermal conductors. The thermal conductivity of operating room tables or return electrodes causes heat to be readily conducted away from a patient when the patient makes contact with the operating room table or return electrode that is within the above temperature range. The transfer of heat from the patient to the operating room table or return electrode causes the patient to feel even colder than the operating room temperature, thereby increasing the patient's discomfort.

Some common solutions for warming patients include the use of heated air or fluid circulation systems. Heated circulation systems can be incorporated into pads that are positioned underneath or on top of a patient during a surgical procedure. The circulation systems commonly include tubes or conduits through which air, water, or another fluid can be circulated. These systems also include a pump to circulate the fluid or air as well as a heating element for heating the air or fluid before it is circulated through the tubes or conduits. While such systems may provide heat to a patient during a surgical procedure, the systems also suffer from drawbacks. For example, heated circulation systems typically do not provide even heating to the patient. Rather, the temperature in the areas directly adjacent to the tubes or conduits is often significantly higher than the areas between the tubes or conduits.

Another common solution for warming patients includes the use of one or more heated blankets. The heated blankets may be draped over a patient or positioned between the patient and the operating room table, for example. The heated blankets may be electric heating blankets or blankets made of cotton or wool that has been warmed in a warming box.

Drawbacks and difficulties are encountered with the use of both electric heating blankets and warmed blankets. For example, blankets warmed in a warming box maintain their temperature for a relatively short period of time. Once they have cooled off, the blankets must be replaced with freshly warmed blankets. It can be inconvenient to replace blankets during an electrosurgical procedure, especially when the blankets must be replaced multiple times during a lengthy procedure. Furthermore, because of the difficulty in moving and repositioning a patient during an electrosurgical procedure, it can be impractical to replace cooled blankets when they are placed between the patient and the operating room table. Additionally, a sterile field must be maintained throughout a surgical procedure. Replacing cooled blankets during a surgical procedure may compromise the sterile field, which can lead to patient infection and other complications. Moreover, blankets that are draped over a patient, whether heated or warmed, may move or fall off of the patient during the procedure, thereby requiring additional attention from operating room personnel.

Cold temperatures are not the only cause of discomfort to patients undergoing electrosurgical procedures. Rather, it is well known in the medical field that patients may develop decubitus ulcers, also known as pressure sores during a prolonged period of immobility. Typically, pressure sores develop in elderly patients who are confined to their beds or otherwise have limited movement. The pressure sores arise in those areas of the patient's body where a prolonged pressure is applied to the patient's tissue, usually over an underlying bony prominence. The prolonged pressure causes ischemic damage and tissue necrosis due to the maintenance of blood pressure above the normal capillary blood pressure of 32 mmHg. Although pressure sores typically occur in those patients who remain in one position for an extended period of time, pressure sores may arise from application of an intense pressure applied over a short period of time, approximately two hours, to a localized area, such as during various surgical procedures.

Generally, to prevent pressure sores a patient is placed upon a pressure reducing mattress or pad during a surgical procedure to reduce or substantially eliminate the forces applied to the sensitive areas of the body where tissue covers underlying bony prominences. One device that may be used to prevent pressure sores in an operational scenario is a foam pad, approximately 3-4 inches in height, which is placed between the operating table and the patient. Although foam pads have many advantages, such as being inexpensive and lightweight, they provide minimal relief to the patient while trapping body heat that may aid in generating pressure sores. Furthermore, by trapping heat the foam pad may aid in increasing the patient's tissue temperature so that during an electrosurgical procedure the tissue temperatures may rise above the six degrees) (6°) Celsius temperature rise threshold established by the AAMI. Additionally, foam pads are typically discarded after a surgical procedure since they are difficult to sterilize and clean. Furthermore, the material forming the foam pad may release lethal fumes if ignited during a fire.

An alternate pressure reducing mattress or pad is a layer of sheepskin placed on the operating table. Unfortunately, sheepskin provides poor protection to the patient and does not effectively distribute the patient's pressure throughout the entire surface upon which they are laying. As with the foam pad discussed above, sheepskin is difficult to sterilize and clean following a surgical procedure.

Yet another type of pressure reducing device is the air inflated mattress that includes a vinyl sleeve filled with air to a desired pressure. Unfortunately, the air mattress must be significantly pressurized to prevent the patient from touching the bottom surface upon which the mattress is placed. In the event the patient touches the bottom surface, there is a chance for development of a pressure sore. Additionally, in order to maintain the required pressure, typically, a pump is connected to the mattress to monitor the pressure of air contained within the mattress and pump additional air into the mattress as required. With a patient placed upon the movable air mattress, which is in turn resting upon an operating table, the patient is lying upon two flexible surfaces. The patient is thereby placed in an unstable and precarious position during surgical procedures. Additionally, air-type mattresses are expensive to maintain due to the need for a pump to maintain the required air pressure. Furthermore, the air mattress may easily be perforated, thereby leaking air and reducing the effectiveness of the mattress to maintain the patient distal from the surface upon which the mattress is placed.

A similar pressure-reducing device to the air filled mattress is the water type mattress. The water-type mattress has a similar form to that of the air mattress; however, water is pumped through the mattress rather than air. Unfortunately, the water type mattress suffers from many of the limitations of the air type mattress. Additionally, in the event that the water mattress leaks, a large amount of water would be discharged onto the floor surrounding the patient, thereby making it dangerous for individuals to walk and work in close proximity to the patient.

Although many of the above-described limitations are alleviated in general use within a hospital, each recited pressure sore device has various drawbacks with respect to their use during electrosurgical procedures. For example, in the event a foam type mattress is used during an electrosurgical procedure, there is a chance that the foam pad may ignite, thereby burning the patient and also emitting lethal fumes within the operating theater.

With respect to the air and water type mattresses, inclusion of the required pumps to maintain the desired pressure for a long period of time increases the amount of equipment necessarily stored within an operating theater. With more equipment within the limited space, the ability of the surgeon to move around is reduced. In the event of a water leak from the water mattress, there is the possibility that of electrocution of the patient and/or the physicians and nurses in the operating theater, as well as the possibility of shorting of the electrosurgical return electrode.

Therefore, it would be an advance in the present electrosurgical art to provide an electrosurgical return electrode that is self-limiting, while increasing the comfort of the patient by providing heating capabilities and reducing the likelihood of pressure sore creation.

BRIEF SUMMARY OF THE INVENTION

The present invention overcomes the shortcomings of the prior art by providing a return electrode that eliminates patient burns without the need for expensive disposable electrodes and monitoring circuits in specialized RF generators, while also providing heating capabilities to warm a patient and minimizing the occurrence of pressure sores for patients having electrosurgical procedures.

Briefly, the improved return electrode according to the preferred embodiments of the invention hereof include an effective surface area that is larger than other return electrodes that have been disclosed or used in surgery previously. It is so large and so adapted for positioning relative to the body of a patient that it eliminates the need for conductive or dielectric gels. Moreover, the exposed surface is of a material that is readily washable, disenfectable, and/or sterilizable so as to facilitate easy and rapid conditioning for repeated use. It employs geometries and materials whose impedance characteristics, at typically used electrosurgical frequencies, are such that it self-limits current densities (and corresponding temperature rises) to safe thresholds, should the effective area of the working surface of the electrode be reduced below otherwise desirable levels. Accordingly, the need for the foregoing expensive monitoring circuits in specialized RF generators is eliminated. Additionally, the improved return electrode includes a heating element to warm a patient in a relatively cold environment. Furthermore, the improved return electrode incorporates one or more pressure sore pads that prevent the formation of pressure sores, while aiding with current transfer between the patient and the return electrode.

In accordance with a feature of the invention, an electrosurgical return electrode is made sufficiently large to present sufficiently low electrical impedance and low current densities at typical electrosurgical frequencies used in medical procedures to reduce the possibility of excessive temperature elevation in adjacent patient tissue, (i.e., by maintaining temperature ("T") rise below six degrees) (6°) Celsius) thereby avoiding tissue necrosis or other undesired patient trauma.

In accordance with yet another feature of the invention, the working surface of the electrode (the electrode surface that is in contact with or in close proximity to the patient) is made sufficiently large in area so that in normal use, current flow will not be reduced to a point where it impedes the surgeon's ability to perform surgery at the surgical site.

In accordance with yet another feature of the invention, the electrosurgical return electrode has a multi-layer construction, including an electrode and one or more pressure sore pads.

In accordance with yet another feature of the invention, in one embodiment, controlled electrical conductivity is imparted to the electrode by the inclusion therein of electrically conductive materials such as conductive threads or carbon black, thus conditioning conductivity as a function of surface area to levels which limit passage of current therethrough to safe values.

In accordance with yet another feature of the invention, in one embodiment, the electrosurgical return electrode includes a pressure sore pad disposed on top of an electrode. As such, the material forming the pressure sore pad acts as, alternatively, a conductive layer or an insulative layer.

In accordance with still another feature of the invention, the electrosurgical return electrode includes heating capabilities to warm a patient during a surgical procedure.

In accordance with another feature of the invention, the electrosurgical return electrode includes two pressure sore pads that aid with the reduction in the creation of decubitus ulcers or pressure sores, and a heating element for providing heating capabilities to warm a patient during a surgical procedure In accordance with yet another feature of the invention, in another embodiment, a moisture impervious working surface is provided for positioning adjacent an adjoining surface of the body of a patient, thus facilitating cleansing and reuse of the electrosurgical electrode.

In accordance with yet another feature of the invention, the aforementioned moisture impervious working surface is made resistant to normally encountered cleaning, disinfecting, and sterilizing agents, thus further facilitating cleansing and reuse.

In accordance with yet another feature of the invention, in another embodiment, a sleeve is provided for cooperative use with the electrosurgical electrode, thus protecting the electrode and the pressure sore pad(s) from inadvertent damage that might occur, for example, from accidental contact of the active electrosurgical instrument with the electrode surface or the pressure sore pad(s).

In accordance with yet another feature of the invention, the electrical impedance of the materials in and adjacent to the working surface of the electrode is sufficiently elevated so as to limit current density at the working surface to a level below the threshold of patient tissue trauma, thus providing a self-limiting characteristic to prevent patient trauma in the event of accidental reduction of the effective working surface of the electrode.

In accordance with yet another feature of the invention, in one embodiment, the electrosurgical electrode is form-fitted to the operating table on which the electrosurgical procedure is to be performed, thus facilitating realization of other features of the invention.

Additional features and advantages of the invention will be set forth in the description which follows, and in part will be obvious from the description, or may be learned by the practice of the invention. These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

The electrosurgical return electrode of the present invention employs geometries and materials whose impedance characteristics, at typically used electrosurgical frequencies, are such that it self-limits current densities (and corresponding temperature rises) to safe thresholds, should the contact area between a patient and an effective working surface of the electrode be reduced below otherwise desirable levels. Additionally, the self-limiting electrosurgical electrode is capable of warming a patient that is positioned on the electrode. Furthermore, the self-limiting electrosurgical electrode is adapted to prevent the formation of pressure sores on a patient while the patient is positioned on the electrode.

To aid with understanding the various aspects and illustrative embodiments and features of the present invention, discussion will first be made with respect to the structures and features of electrosurgical electrodes that provide self-limiting characteristics. Following such discussion, a detailed description of illustrative embodiments of a self-limiting return electrode with heating and pressure sore prevention capabilities will be provided. An electrosurgical return electrode having heating and/or pressure sore prevention capabilities integrally formed therein allows one device to include self-limiting characteristics necessary to electrosurgical procedures, while increasing the comfort of the patient. In this manner, the novel electrosurgical electrode of the present invention protects a patient from being burned during an electrosurgical procedure, warms the patient in a relatively cold environment, and prevents pressure sores from forming.

Figure 1:
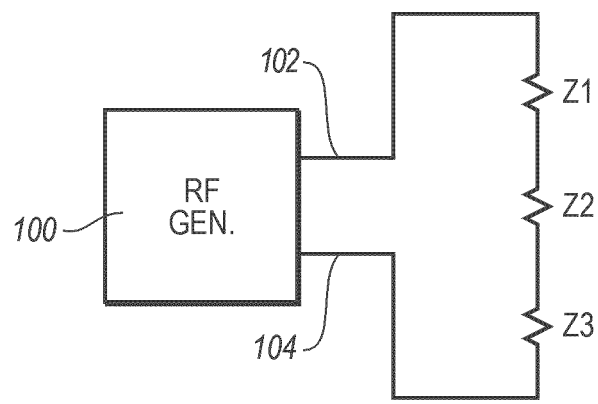
FIG. 1 is a simplified electrical schematic diagram illustrating typical impedances effectively included in the operative path of radio frequency current flow as presented to an electrosurgical generator during an operative procedure.

Now turning to the drawings, and more particularly FIG. 1 thereof, it will be seen to depict a simplified electrical schematic diagram illustrating typical impedances effectively included in the operative path of radio frequency current flow as presented to an electrosurgical generator during an operative procedure. There, it will be seen are conventional radio frequency electrical power generator 100, such as but not limited to constant power, voltage, and/or current or variable power, voltage and/or current generators. Connected to electrical power generator 10 are conventional electrical conductors 102 and 104 which respectively connect generator 100 to the surgeon's implement represented by impedance $z_1$ and an electrosurgical return electrode represented by impedance $z_3$. Impedance $z_2$ is provided to represent the impedance presented by the patient's tissue lying between the operation site and the return electrode. Electrical conductors 102 and 104 are representative of one illustrative structure that is capable of performing the function of connecting means for making electrical connection to the return electrode. It may be appreciated by one skilled in the art, however, that various other structures are appropriate and capable of performing the desired function.

Although the diagram of FIG. 1 is simplified and generally considers circuit elements in terms of the principal resistances, including the reactants contributed by the surgical instrument, the patient's body and the return electrode, so as to clearly and succinctly illustrate principles of the invention, it should be understood that in reality certain other parameters would be encountered, parameters such as distributed inductance and distributed capacitance which, for purposes of clarity in illustration of the principles hereof, are deemed relatively small and so not considered at this point in this description. However, as set forth below, in one embodiment when an insulating sleeve is interposed between the electrode and the body of a patient, a significant element of capacitive reactance may be included in the impedance of $Z_3$. It should also be noted that FIGS. 1-10 are intentionally simplified so as to present the principles of the invention succinctly. The discussion of FIGS. 11-17 includes a more detailed and complete description of the self-limiting features of the invention, including the theoretical basis and exemplary geometries and materials used to achieve the self-limiting features.

The initial embodiment, hereof, is that of an electrode operating in a combined resistive and/or capacitive mode. Accordingly, if the relatively small stray capacitive and inductive reactants are disregarded, the total effective impedance of the circuit will be equal to the sum of the individual impedances $z_1$, $z_2$ and $z_3$; and since essentially the same current will pass through all three, the voltage generated by RF generator 100 will be distributed across impedances $z_1$, $z_2$, and $z_3$ in direct proportion to their respective values. Thus, the energy released in each of such components will also be directly proportional to their values.

Since it is desired that developed energy be concentrated in the region where the surgeon's implement contacts the patient's tissue, it is desirable that the resistive component of the impedance represented by $z_1$ be substantial and that current passing therethrough (and consequent energy release) be concentrated in a very small region. The latter is accomplished by making the region of contact with the patient at the operative site very small.

It is known that, in contrast with the foregoing series circuit, components of combined resistive and capacitive reactance, when connected in parallel, present a total effective impedance that is given by the formula:

$$z_{\mathit{eff}} = \frac{1}{\frac{1}{z_1}+\frac{1}{z_2}+\frac{1}{z_3}+\frac{1}{z_4}+\frac{1}{z_5}+\frac{1}{z_6}} \quad (1)$$

Thus, if 100 similar impedances, each of 100 ohms, were connected in parallel, the effective impedance $Z_{\mathit{eff}}$ would equal one ohm. If half of such impedances were effectively disconnected, the remaining effective impedance would be two ohms, and if only one of the impedances were active in the circuit, the remaining effective impedance would be 100 ohms. The significance of these considerations and their employment to render the electrode hereof self-limiting and fail-safe will be evident from the following description of the elements illustrated in FIGS. 2A, 2B, 2C, and 3.

Figure 2A:
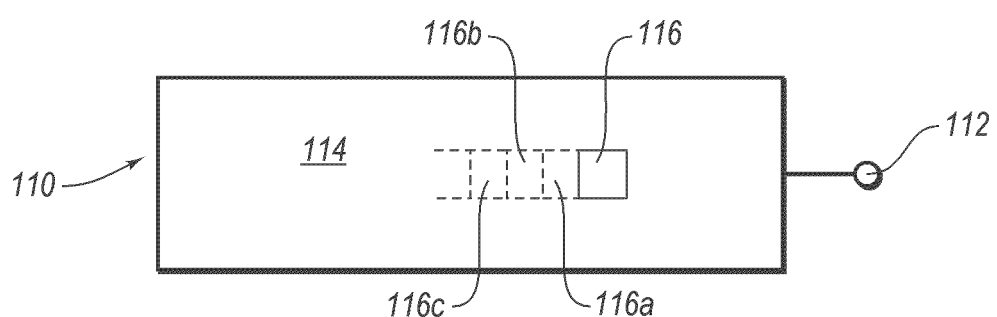
FIG. 2A is a top view of a wide-area distributed electrosurgical return electrode illustrating the principles of the invention.

Now turning to FIG. 2A, there will be seen a schematic representation of the top view of a wide-area distributed electrosurgical return electrode 110 illustrating the principles of the invention. At the right hand side of the figure there is shown an electrical connection terminal 112 to facilitate connection to an electrical return conductor, such as conductor 104 of FIG. 1.

The surface 114 of return electrode 110 is preferably smooth and homogeneous and includes a thin resistive and/or dielectric layer. Alternatively, surface 114 of return electrode 110 may include a capacitive and/or inductive layer, depending on the particular operation of return electrode 110. For instructional purposes of this description and to aid in the mathematical modeling of return electrode 110, electrode 110 may be thought of as including a plurality of uniformly-sized regions or segments as represented by regions 116, 116a, 116b, 116c . . . 116n. It will be appreciated by one skilled in the art, however, that return electrode 110 may or may not include discontinuous regions or segment, it being preferred that electrode 110 have continuous segments.

Figure 2B:
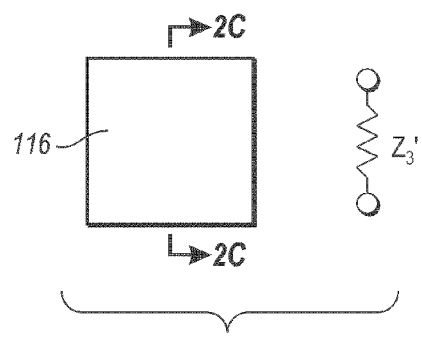
FIG. 2B is an enlargement of a segment of the electrosurgical return electrode of FIG. 2A.

Region/segment 116 is shown larger in FIG. 2B in order to be similar in scale to the resistive impedance $z_3'$ it represents. It thus will now be evident that each of the segments of electrode 110 corresponding to segments 116 . . . 116n inherently has the capability of presenting an impedance similar to that of impedance $z_3'$. However, the number of such segments which are effectively active in parallel within the circuit is a direct function of the surface area of the patient that overlies the electrode. Thus, in the case of a large supine patient whose body is in effective contact with 50 percent (50%) of the upper surface of the electrode, 50 percent of the segments corresponding to segments 116-116n will be effectively paralleled in the circuit to form an impedance represented by impedance $z_3$ of FIG. 1; and, accordingly, if electrode 110 contains 100 segments of 100 ohms each, the effective impedance operatively presented by the effective 50 percent of the electrode elements would be 2 ohms. Since 2 ohms is very small compared with the impedance represented by elements $z_1$ and $z_2$, very little energy is lost at the region of contact between the patient and the electrode, and due also to the relatively large effective working area of the electrode, current density and temperature elevation are maintained below the danger thresholds mentioned above.

Now, if for any reason, the effective contact area between the patient and electrode were to be reduced to the surface of only one of the segments 116-116n, then the effective impedance (combined capacitive reactance and resistance in the example under consideration) would increase to 100 ohms; and at some point of reduction in contact area, the effective impedance would rise to a level relative to the impedance presented at the site of the electrosurgical instrument so as to diminish the electrosurgical effect of the surgical instrument or otherwise prevent effective use of the instrument by the surgeon, thus signaling the surgeon that the patient should be repositioned so as to present a greater surface area in contact with the return electrode. At the same time, the total circuit impedance would be increased so that the total current that would flow if the surgeon attempted to employ his instrument without repositioning the patient would be reduced to a value below that which would cause undesired trauma to the patient. Accordingly, there is provided a self-limiting feature that enhances safety in use without the need for the aforementioned separate circuit monitoring and control circuits.

Figure 2C:
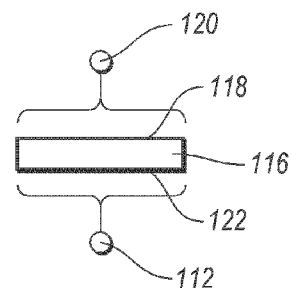
FIG. 2C is a cross section taken along the section lines 2C-2C of FIG. 2B and illustrating the effective circuit impedance represented by the segment of 2B.

FIG. 2C is a cross section taken along the section lines 2C-2C of FIG. 2B and illustrates the effective circuit impedance $z_3$ represented by the segment 116 of 2B. There, in FIG. 2C are seen small segment 116 with its upper patient-contacting surface 118 represented electrically by terminal 120 and its lower surface 122 represented by electrical terminal 112. For the purpose of this description (and in order to present the principles underlying this embodiment clearly), the impedance $z_3$ may be thought of as existing between terminals 120 and 112. Of course, it will be evident to those skilled in the art that in an embodiment in which a thin but highly conductive layer is included along the lower surface of electrode 110, each of the impedances represented by the remaining segments are connected at their lower extremities in parallel to terminal 112; whereas, if such highly conductive layer is absent, then, in addition to the impedance represented by the material lying between the upper and lower regions of each segment, there will be an additional impedance (not shown) that is represented by the material through which current would have to pass transversely or laterally through the electrode in order to get to terminal 112.

It should now be evident that if lateral impedance is minimized by provision of the aforementioned thin conducting layer, or if the effective conductivity at the lower part of the material of region 116 is otherwise increased, the effective impedance presented by the return electrode will be inversely proportional to the effective upper surface of the electrode that is in contact with a patient.

Figure 3:
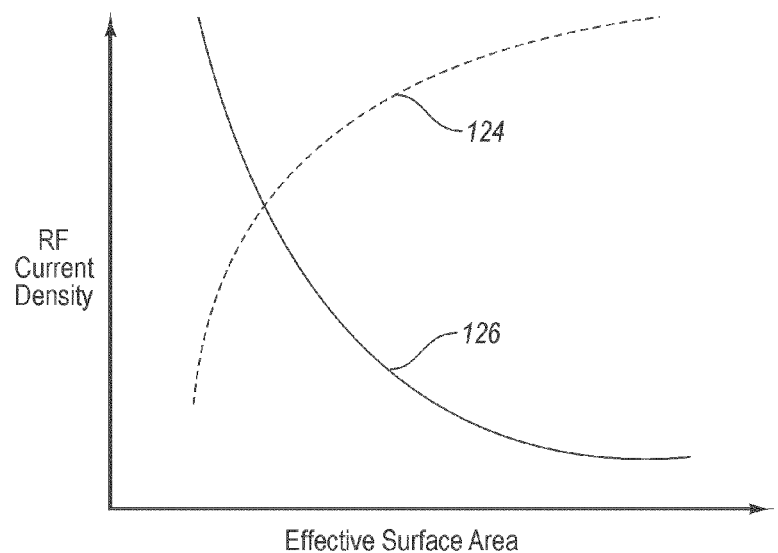
FIG. 3 is a chart illustrating in graphical form the relationships between effective surface area of the return electrode and the effective radio frequency current density developed at the electrode.

FIG. 3 is a chart generally illustrating in graphic form the relationships between the effective surface area of the return electrode and the effective radio frequency current densities developed at the electrode. However, before proceeding to a consideration of such chart, it should be noted that the chart is simplified so as to illustrate the principles underlying the invention and does not represent actual data that may vary substantially. In FIG. 3 there is seen a plot of RF Current Density versus Electrode Effective Surface Area, the latter (as should now be evident to those skilled in the art) being that part of the surface of the return electrode that makes effective electrical contact with the body of a patient. As would be expected from the foregoing discussion, when the effective area is large, the current at the surgeon's implement is high (dashed graph line 124) and the corresponding current density across the return electrode is very low (solid graph line 126). This is, of course, the condition desired for conducting electrosurgery. However, if we assume constant current throughout the circuit, as the effective surface area decreases, the current density across the return electrode (solid graph line 126) increases with a corresponding decrease in the current at the surgeon's instrument (dashed graph line 124).

When the effective surface area declines to some predetermined point, there will remain insufficient current at the surgical instrument to effectively conduct electrosurgery.

It may be appreciated by one skilled in the art that the change in current density and available current to the surgeon may or may not occur simultaneously with the variations in effective surface area. Various embodiments of the present invention may have substantially simultaneous changes in current density and available current, while other embodiments of the present invention may include a lag period therebetween.

The parameters selected for the materials and electrode dimensions are chosen so that current density and corresponding tissue temperature elevation adjacent the return electrode do not exceed the limits mentioned in the introduction hereof. It will now be seen that by a proper selection of such parameters the return electrode is made self-limiting, thereby obviating the need for the additional monitoring circuits to which reference is made above.

To facilitate description of the principles underlying the invention, the foregoing is described in terms of impedances whose principal components are resistances and capacitive reactants. However, the principles of the invention are also applicable to other embodiments in which the impedances include any combination of resistive, capacitive and/or inductive impedances.

The invention hereof is now further described in connection with applications in which an effective dielectric layer is represented by, for example: (i) a physical dielectric layer on the upper surface of the electrode; (ii) the material of a surgical gown worn by the patient; (iii) a bed sheet or other operating room linens interposed between the patient and the return electrode; (iv) the material of a protective sleeve fitted over the return electrode; (v) or any combination thereof.

Figure 4:
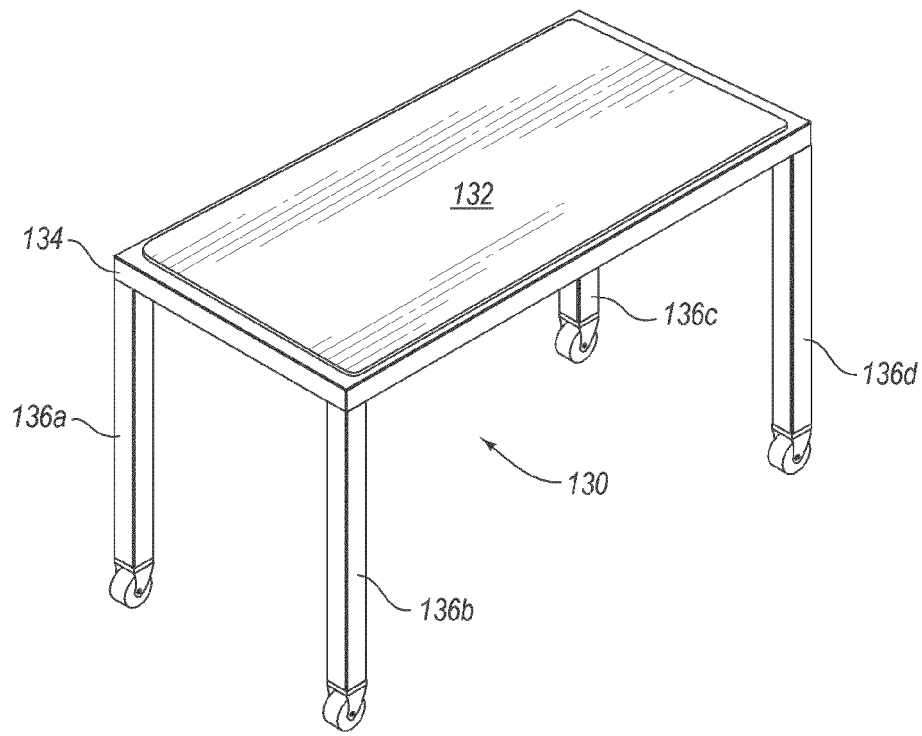
FIG. 4 is a perspective view showing an operating table with the electrosurgical return electrode according to the invention disposed on the upper surface thereof.

Reference is now made to FIG. 4, which illustrates in perspective an operating table 130 with an electrosurgical return electrode 132 according to the invention disposed on the upper surface thereof, an edge of table 130 being identified by reference number 134. Operating table 130 is shown to have conventional legs 136a-136d that may be fitted with wheels or rollers as shown. Table 130 is one structure that is capable of performing the function of supporting means for supporting a patient during treatment. It may be appreciated by one skilled in the art, however, that various other configurations of support means are possible and capable of performing the required function. For example, supporting means may include but not be limited to chairs, plates, beds, carts, and the like.

Figure 5:
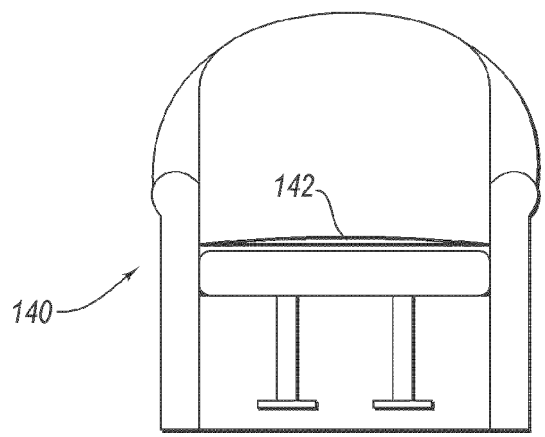
FIG. 5 is a front view illustrating a surgical chair with an electrosurgical return electrode according to the invention disposed on the surface of the seat thereof.

Although, in FIG. 4, the entire upper surface of table 130 is shown as being covered with return electrode 132, it should be understood that entire coverage is by no means required in order to practice the principles of the invention. Thus, when used with conventional electrosurgical generators, the return electrode needs only to present an effective working surface area which is sufficient to provide adequate resistive, capacitive, or inductive coupling at the typically employed RF frequencies so as not to interfere with the surgeon's ability to perform surgery while at the same time avoiding undesired tissue damage. It has been found that at conventional electrosurgical frequencies, this has necessitated only an effective working surface area no larger than about the projected outline of one-half of the torso for an adult patient lying on an operating table or the buttocks of a patient sitting in a chair such as is illustrated in FIG. 5. However, the effective working surface area will vary depending on the material used, in some geometrical configurations, and in instances where various layers of operating room linens are placed over the electrode. The principles hereof may be successfully employed and the effective working surface area of the return electrode determined in such circumstances by routine experimentation. Under certain conditions, the effective working surface may be as small as about seven square inches (or about 45 square centimeters).

Moreover, although the return electrodes shown in FIGS. 6-8 and 10 are depicted as being rectangular in shape, it will be evident that they could be oval or contoured as, for example, to follow the silhouette of the torso or other principal part of the body of a patient. As will be evident from the foregoing, it is important that the electrode be configured so that when the electrode is used: (1) the return current density on the surface of the patient is sufficiently low; (2) the electrical impedance between the electrode and the patient is sufficiently low so that electrical energy is not concentrated sufficiently to heat the skin of the patient at any location in the electrical return path by more than six degrees) (6°) Celsius; and (3) the characteristics of the materials and geometries are such that if the effective area of the electrode is reduced below a selected threshold level, there will be insufficient energy dissipated at the surgeon's implement for him to continue effectively using the implement in its electrosurgical mode.

As will be recognized by those skilled in the art, it is not necessary for there to be direct ohmic contact between the skin of a patient and the return electrode hereof for the electrode to perform generally according the foregoing description, for although capacitive reactance (represented by the distance between a patient's body and the electrode) will be introduced if something such as a surgical gown separates them, such capacitive reactance will modify rather than destroy the impedance identified as $z_3$.

As is known to those skilled in the art, in an alternating current circuit (e.g., such as those used in electrosurgery) the capacitive reactance of an impedance is a function both of capacitance and the frequency of the alternating current electrical signal presented to the reactance. Thus, the formula for capacitive reactance (in ohms) is:

$$Xc = \frac{1}{2\pi fC} \qquad (2)$$

where Xc is capacitive reactance in ohms, $\pi$ is 3.14159, f is frequency in hertz, and C is capacitance in farads.

The formula for capacitance in a parallel plate capacitor is:

$$C = \frac{\kappa \varepsilon_0 A}{t} \qquad (3)$$

where C is capacitance in Farads, $\kappa$ is the dielectric constant of the material lying between the effective plates of the capacitor, A is the area of the smallest one of the effective plates of the capacitor in square meters, t is the separation of the surfaces of the effective plates in meters, and $\varepsilon_0$ is the permittivity of air in Farads/meter. Thus, it will be seen that to meet maximum permissible temperature rise criteria in an embodiment in which electrode circuit capacitance is substantial, different minimum sizes of electrodes may be required depending upon the frequency of the electrical generator source, the separation of the body of the patient from the electrode, and the material lying between the effective conductive region of the electrode and the adjacent body surface. Accordingly, although the principles of the invention are applicable to a wide range of frequencies of electrosurgical energy, the considerations set forth herein for minimum sizes of return electrodes specifically contemplate frequencies typically employed in conventional electrosurgical energy generators.

Those skilled in the art know that, with the currently used disposable return electrodes, reducing the effective size of the electrode to about three square inches will not reduce the RF current flow to a level where it will impede the surgeon's ability to perform surgery nor concentrate current to a level to cause patient trauma. However, to provide for some spacing of the electrode from patient's body, a return electrode according to the invention hereof, would need a minimum effective area of between about 7 and about 11 square inches (about 45 $cm^2$ to about 70 $cm^2$) with a relatively small separation from the skin of the patient such as that provided by a surgical gown or no interposing gown at all. Such an effective area is easy to obtain if the patient is positioned on an electrode that is the size of their upper torso or larger.

The characteristics of the desired dielectric for the present embodiment are sufficiently comparable to those of selected rubbers, plastics and other related materials that the latter may be satisfactorily employed as materials for the return electrode. As mentioned above, with such a return electrode, if the patient is positioned such that not enough of the return electrode is in close proximity to the patient to result in as low impedance as needed, the results would be that the current flow from the electrosurgical generator would be reduced to a level making it difficult for the surgeon to perform surgery. Thus, in the present embodiment, notwithstanding interposition of some additional capacitance represented by a surgical gown, the features described above will continue to occur.

As mentioned above, FIG. 5 is a front view illustrating a surgical chair 140 with an electrosurgical return electrode 142 according to the invention disposed on the upper surface of the seat thereof. Accordingly, when a patient is sitting in the chair, the buttocks and upper part of the thighs overlie and are in sufficiently close proximity to return electrode 142 so that coupling therebetween presents an impedance meeting the foregoing criteria; namely, that the electrical impedance between return electrode 142 and the patient is sufficiently low to allow the surgeon to perform the procedure while providing that current density is sufficiently low and that insufficient electrical energy is developed across return electrode 142 to heat the skin of the patient at any location in the electrical return path by more than six degrees) (6°) Celsius.

Figure 6:
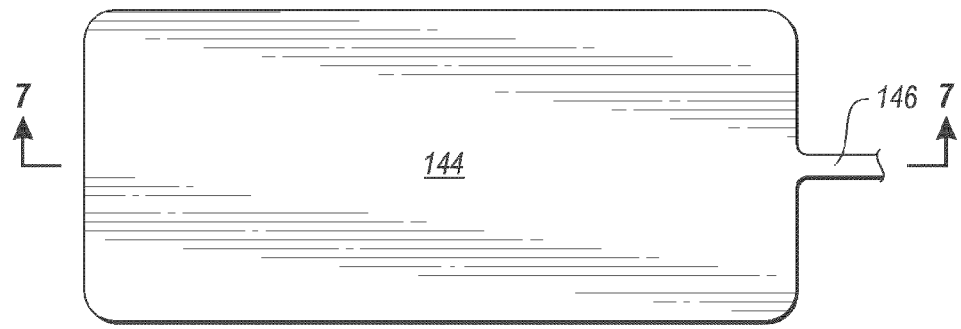
FIG. 6 is a top view of an electrosurgical return electrode according to the invention.

FIG. 6 is a top view of another electrosurgical return electrode according to the invention. It will be observed that the upper exposed, or working, surface of the electrode again is expansive so as to meet the foregoing criteria for low impedance. Although it is not necessary that the electrode cover the entire surface of an operating table or the entire seat surface of a dental or other patient chair, it has been found advantageous in some instances to provide a greater surface area than that of the projected area of the buttocks or torso of a patient so that if a patient moves position during the course of a procedure, a sufficient portion of the patient will remain in registration with the electrode surface so that the effective impedance will remain less than the above-described level.

At this juncture, it may be helpful to emphasize characteristics of the improved electrode according to the invention hereof that are deemed particularly relevant to an understanding of the inventive character thereof. First, as mentioned above, the electrode does not need to be in direct contact with a patient, either directly or through intervening conductive or nonconductive gel. In addition, because of its expansive size, there is no need for tailoring the electrode to fit physical contours of a patient. In this connection, it has been found that although with selected materials and geometries, the self-correcting and self-limiting principles hereof could be achieved in an electrode as small as about seven square inches (or about 45 square centimeters) in working surface area, the preferable range of exposed upper working surface area of the electrode lies in the range of from about 11 to 1,500 square inches (or about 70 to 9,680 square centimeters). By making the electrode several times larger (typically, at least an order of magnitude larger) in working surface area than previous proposals, the need for direct physical attachment, either directly to the skin of the patient or through gels, is eliminated.

The electrode according to the invention hereof, as illustrated in FIG. 6, may be made of conductive plastic, rubber, or other flexible material which, when employed in the electrode will result in an effective dc resistance presented by each square centimeter of working surface to be greater than about 8000Ω. Silicone or butyl rubber has been found to be particularly attractive materials as they are flexible, as well as readily washable and sterilizable. Alternatively, the main body of the return electrode may be made of inherently relatively high resistance flexible material altered to provide the requisite conductivity. A preferred example of the latter is that of silicone rubber material in which there are impregnated conductive fibers, such as carbon fiber, or in which there have been distributed quantities of other conductive substances such as carbon black, quantities of gold, silver, nickel, copper, steel, iron, stainless steel, brass, aluminum, or other conductors.

Further reference to FIG. 6 reveals the presence of a conventional electrical connector 146 attached to the electrode 144 to provide a conventional electrical return to the electrosurgical radio frequency energy source (not shown). Connector 146 is another structure capable of performing the function of connecting means for making electrical connection to the return electrode. Connector 146 is only illustrative of one possible structure for performing the desired function; it being appreciated by one skilled in the art that various other structures are capable of performing the required function.

Figure 7:
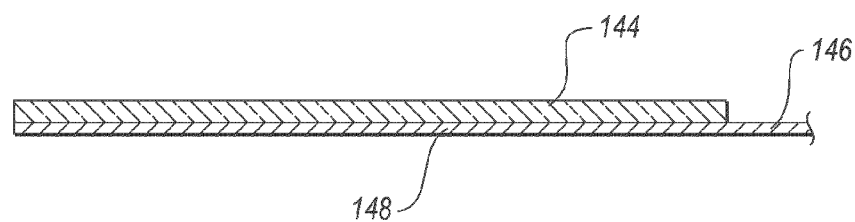
FIG. 7 is a section taken along the lines 7-7 of FIG. 6.

As mentioned above, FIG. 7 is a section taken along the lines 7-7 of FIG. 6. FIG. 7 shows an electrode 144 similar to electrode 110 of FIGS. 2A-2C, except that electrode 144 includes a thin highly conductive lower stratum 148 to facilitate conduction of current outwardly to terminal 146. In one preferred form, the thickness of the electrode lies in a range from about ⅛₂ inch to ¼ inch (about 0.08 cm to 0.64 cm), which, with the aforementioned range of impedance of the main body of material and the capacitive reactance of the upper dielectric layer, provides the required impedance together with desired physical flexibility for ease of use and handling.

Figure 8:
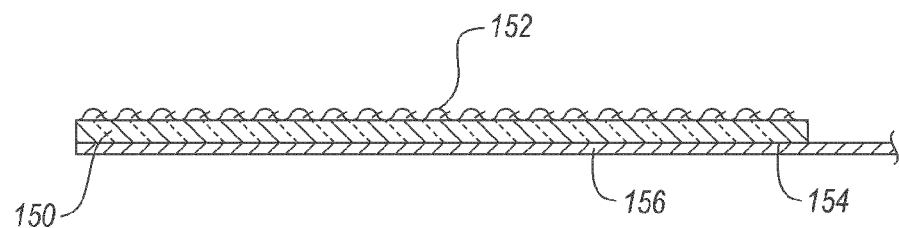
FIG. 8 is a section similar to that of FIG. 7 but illustrating the capacitance presented by a patient's surgical gown.

FIG. 8 is a section similar to that of FIG. 7, but presenting a multiple layer embodiment illustrating the separation presented by a patient's gown according to the invention hereof. There, in FIG. 8 are shown a layer 150 (similar to layer 144 of FIG. 7) and an overlying effectively capacitive layer 152 representing an insulating dielectric layer, a pressure sore pad, a patient's surgical gown, an operating room linen, a protective sleeve or sheath, or any combination thereof. It should be understood that in addition to a construction similar to that of the electrode of FIGS. 6-7, a conductive layer 154 of FIG. 8 could comprise a sheet or screen of gold, brass, aluminum, copper, silver, nickel, steel, stainless steel, conductive carbon, conductive fluids, gels, saline, and the like. Further reference to FIG. 8 reveals another dielectric layer 156 covering the lower surfaces of layer 150.

Figure 9:
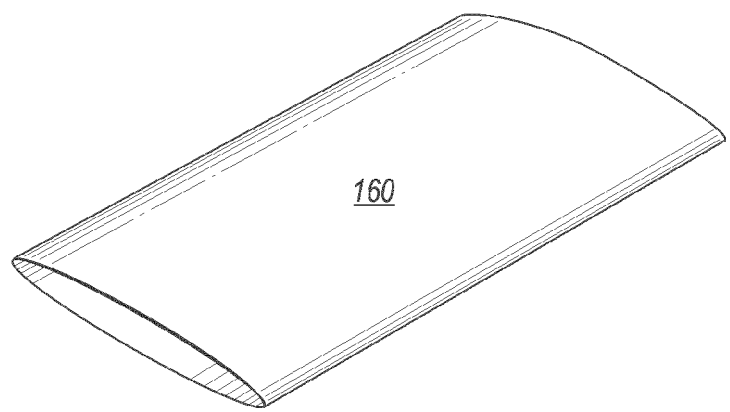
FIG. 9 is a perspective view of a cover adapted for encasing any of the embodiments of FIGS. 6-8.

FIG. 9 is a perspective view of a sleeve 160 adapted for encasing any one of the embodiments of FIGS. 6-8. Thus, provision is optionally made for encasing the foregoing return electrode-shaped electrodes within protective envelopes in situations in which it is desired to eliminate the need for cleaning the electrode itself by protecting it from contamination through the use of a sleeve of impervious material from which the electrode, after use, can merely be withdrawn and the sleeve discarded. As will be evident to those skilled in the art, such a sleeve may preferably be made of any of a variety of known materials, such as vinyl plastics, polyester or polyethylene.

Figure 10:
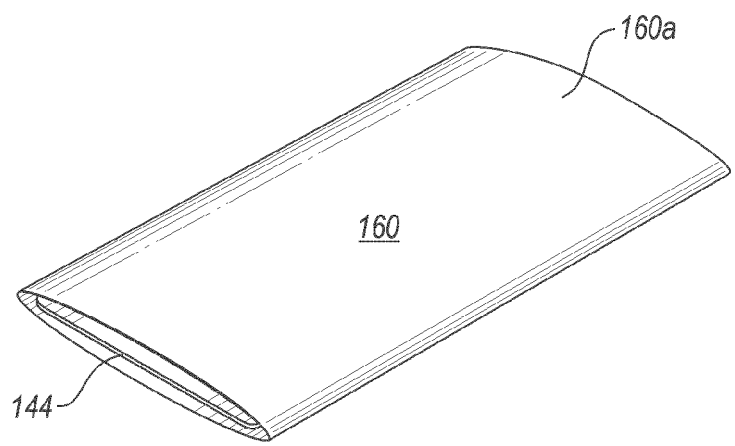
FIG. 10 is a view illustrating one of the embodiments of FIGS. 6-8 encased within the cover of FIG. 9.

FIG. 10 is a view illustrating one of the embodiments of FIGS. 6-8 encased within the sleeve of FIG. 9. There, it will be seen, is outer surface 160a of sleeve 160; and shown encased within sleeve 160 for illustrative purposes is electrode 144 of FIG. 6.

Total Electrode Ground Pad Impedance and Self-Limiting Feature

Figure 11:
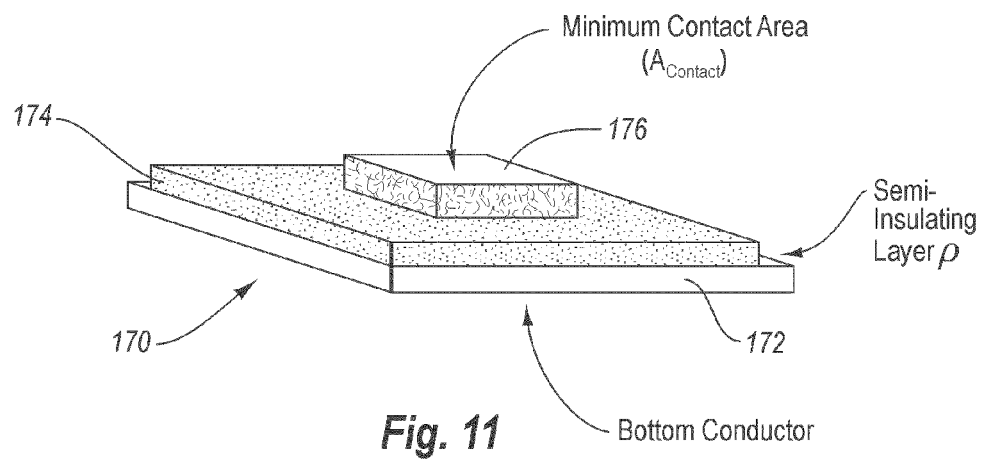
FIG. 11 is a perspective view of an electrode according to the invention illustrating a simulated condition when the effective contact area with a patient is substantially less than the physical electrode size.

FIG. 11 depicts an electrosurgical electrode 170 consisting of a conductive metal backing 172 and a semi-insulating layer 174. The electrode 170, and more specifically, semi-insulating layer 174, is in contact with another conducting layer 176 which represents a patient thereupon. The self-limiting feature of electrosurgical return electrode 170 (maintains current densities below a threshold level) arises due to the total impedance of electrode 170, whether such impedance arises from semi-insulating layer 174 alone or in combination with conductive metal backing 172 and/or conducting layer 176. Furthermore, the total impedance may arise from the various resistive, inductive, and/or capacitive components of conductive metal backing 172, semi-insulating layer 174 and/or conducting layer 176.

Electrode 170, which includes a single layer of semi-insulating material 174, has a bulk resistivity $\rho$ and thickness t. An area A placed between a conductive surface and the patient may be modeled as a resistor (R) in parallel with a capacitor (C).

For ease of explanation, we will determine the resistive requirements of electrode 170 for self-limiting in a purely resistive scenario where electrode 170 is modeled as a resistor in parallel with a capacitor. Following the calculation of the minimum requirements for self-limiting in the purely resistive case, we will generalize the analysis for any impedances, whether such impedances result from resistive, capacitive, and/or inductive components.

As such, the resultant total impedance equivalent for the resistor in parallel with the capacitor combination is:

$$Z_{tot} = R \| X_c = \frac{(R)\left(\frac{1}{j\omega C}\right)}{(R)+\left(\frac{1}{j\omega C}\right)} = \frac{R}{1+j\omega CR} \tag{4}$$

where j is an imaginary component of reactance, and $\omega$ is the angular frequency and is defined as $\omega=2\pi f$, where f is the electrosurgical generator frequency. The magnitude of the impedance is:

$$|Z_{tot}| = \sqrt{\frac{R^2}{1+\omega^2 C^2 R^2}} = R\sqrt{\frac{1}{1+\omega^2 C^2 R^2}} \tag{5}$$

Substituting the dependence of R and C on the area A, thickness t, bulk resistivity $\rho$, and the dielectric constant of the material $\kappa$ defined by:

$$R = \frac{\rho t}{A} \tag{6}$$

and $$C = \frac{\kappa \varepsilon_0 A}{t} \tag{7}$$

where permittivity constant $\varepsilon_0 = 8.85 \times 10^{-12}$ F/m, the magnitude of the total impedance is given by:

$$|Z_{tot}| = \frac{\rho t}{A}\sqrt{\frac{1}{1+\omega^2\left(\frac{\kappa\varepsilon_0 A}{t}\right)^2\left(\frac{\rho t}{A}\right)^2}} = \frac{\rho t}{A}\sqrt{\frac{1}{1+\omega^2\kappa^2\varepsilon_0^2\rho^2}} \tag{8}$$

According to the AAMI standard, the total impedance of the electrosurgical electrode should be less than 75Ω under normal operating conditions. It is preferred, therefore, that:

$$\frac{\rho t}{A}\sqrt{\frac{1}{1+\omega^2\kappa^2\varepsilon_0^2\rho^2}} \leq 75\Omega \tag{9}$$

We define $\beta$ as $$\beta = \frac{Z_{tot}}{75\Omega} \tag{10}$$

If $\beta \ll 1$, the electrode will have very low impedance compared to the AAMI standard, and the surgeon will not notice any degradation in the electrosurgical cutting power due to the electrode. If $\beta \gg 1$, the electrosurgical electrode will present such a large impedance that the surgeon will no longer be able to perform electrosurgery. Using $\beta$ in the above inequality, the expression becomes the equality:

$$\frac{\rho t}{A}\sqrt{\frac{1}{1+\omega^2\kappa^2\varepsilon_0^2\rho^2}} = 75\beta \tag{11}$$

It is preferred that self-limiting occurs when the electrode has a large electrode area in contact with the patient (see FIG. 15); however it is also necessary for self-limiting to occur when the patient only makes contact with a small fraction of the total electrode area (see FIG. 11). For self-limiting to work properly, it is necessary for the current density (given by I/A), where I is the total current through the contact area A of the electrosurgical return electrode, to not exceed a critical value $$\left(\frac{I}{A}\right) \leq \left(\frac{I}{A}\right)_{critical} = 100 \text{ mA/cm}^2 \tag{12}$$

AAMI standards indicate that normal electrosurgical currents are on the order of 500-700 mA. If we set 1000 mA=$I_{max}$ as a safe upper limit as to what one might expect for an above average power surgery, then, in order to return the current to the electrode without exceeding $I_{critical}$, the contact area $A_{contact(min)}$ for traditional electrosurgical return electrodes must have a minimum size:

$$A_{contact(min)} \geq \frac{I_{max}}{\left(\frac{I}{A}\right)_{critical}} = \frac{1000 \text{ mA}}{100 \text{ mA/cm}^2} = 10 \text{ cm}^2 \quad (13)$$

It can be appreciated that $I_{max}$ may vary from patient to patient due to changes in the amount of time that the electrode is in contact with the patient, the electrical characteristics of the patient's skin (i.e., resistivity, and the like), the amount of heat being conducted by the patient, the patient's initial skin temperature, and the like. With an electrosurgical return electrode designed according to the prior art, in the event that the contact area with the patient reduces below the $A_{contact(min)}$, while maintaining the $I_{max}$, a burn may result because $(I/A)_{critical} > 100$ mA/cm$^2$, which is the burn threshold. In contrast, the present invention limits the possibility of a burn caused from a reduction of the contact area below $A_{contact(min)}$, while also preventing electrosurgical procedures when the contact area is significantly reduced. Therefore, by selecting the appropriate impedance of electrode 170, the current I is always reduced below $I_{max}$ when $A < A_{contact(min)}$.

Figure 12:
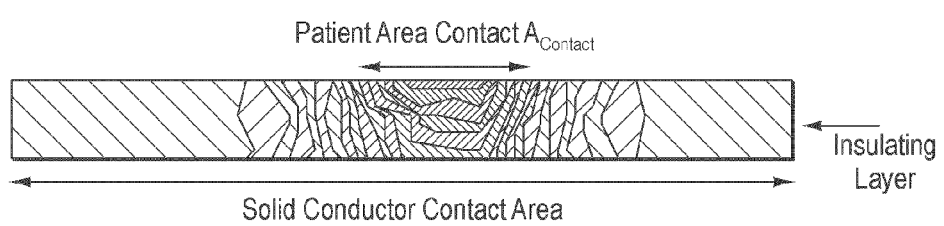
FIG. 12 is a view illustrating current flow density within the electrode when the effective patient contact area is much smaller than the total electrode area.

As such, the impedance between the small electrode with area $A_{contact(min)}$ and the larger metal foil is not simply:

$$R = \frac{\rho t}{A_{contact(min)}} \quad (14)$$

as current can flow through the areas not directly below the patient contact area $A_{contact(min)}$ (FIG. 12). Approximately 10-20% more current flows through the patient contact area $A_{contact}$ than one would expect if the total area of the insulating layer were $A_{contact(min)}$. Equivalently, the effective impedance of the electrode is 10-20% less than what one would normally expect if these edge effects were not present resulting in additional current flow.

As previously mentioned, FIG. 12 reveals current flow distribution through the semi-insulating part of the electrode when the upper contact area with the patient is much smaller than the total electrode surface area. As depicted, current flows through parallel paths around the contact region thus reducing the overall impedance to current flow and thereby increasing the effective area about 10-20 percent. In the Figure, the opaque or heavily hatched region denotes heavier current flow, and the lighter or lightly hatched region denotes lesser current flow.

In order for the electrode to be self limiting, and as efficacious as defined by the AAMI standard, it is preferred that $A_{contact(min)}$ have a value from about 7 cm$^2$ to about 22 cm$^2$, and more preferably about 10 cm$^2$ for electrosurgical currents between 100 mA and about 2,000 mA. Similarly, it is preferred that β range from about 10 to about 50, and more preferably have a value of about 10. Using the various values for $A_{contact(min)}$ and β, it is preferable to solve Equation 11 for the thickness t as a function of the bulk resistivity ρ at different electrosurgical generator frequencies Ω, while inserting a factor of 1.2 to account for the edge effects described above. In the particular illustrative embodiment discussed herein, the factor of 1.2 is included within the resistivity and reactance terms of the equation; however, it may be appreciated by one skilled in the art that the factor of 1.2 is geometry dependent for both the resistive and reactance terms and may vary. Additionally, the value of 1.2 is based on the illustrative geometry of the presently described self-limiting electrode and may vary as the geometry of the electrode varies to account for the different edge effects.

The resulting equation (which identifies and defines the interrelationships of parameters affecting self-limitation) is:

$$t = \frac{1.2A(75\beta)\sqrt{1 + \omega^2\rho^2\kappa^2\varepsilon_0^2}}{\rho} \quad (15)$$

Figure 13:
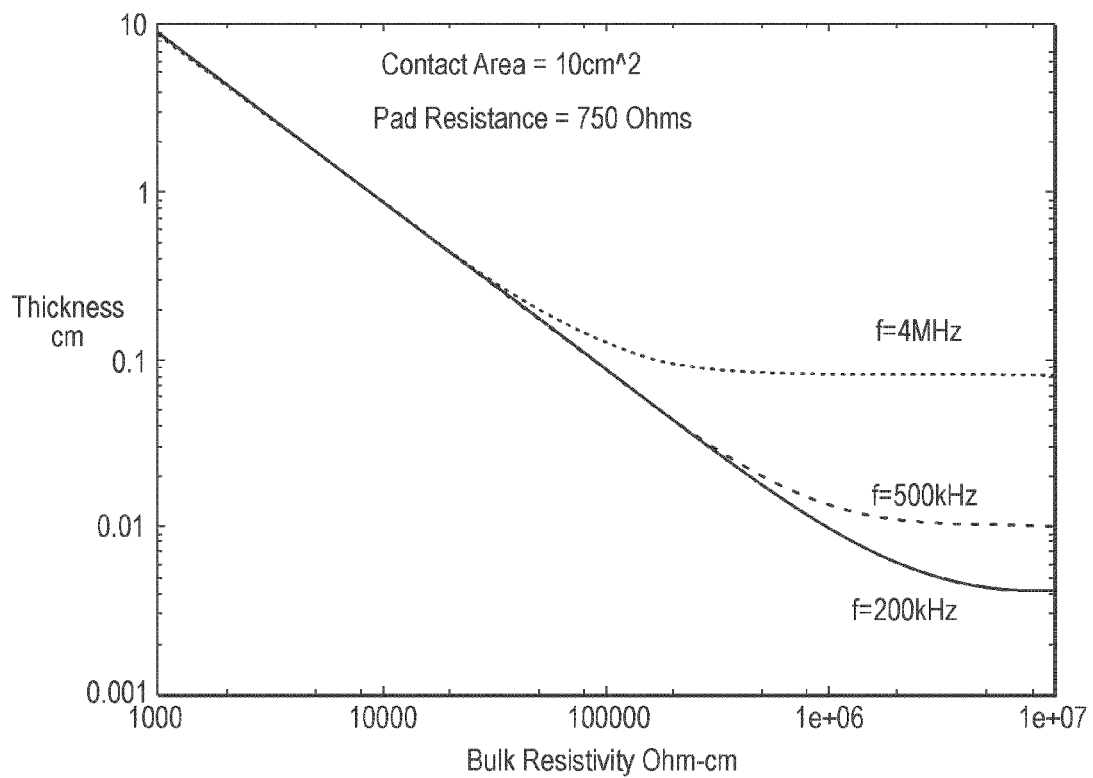
FIG. 13 is a graph depicting variations of bulk resistivity of a resistive layer as a function of electrode thickness for different electrosurgical generator frequencies.

Using Equation 15, FIG. 13 illustrates the variation of minimum bulk resistivity, with electrode thickness, requiring κ=5. The maximum electrode thickness one would imagine using would range from about 0.5 to about 4 inches (about 1.3 cm to about 10.2 cm) and more preferably about 1 inch thick (about 2.5 cm). Above these thicknesses, the electrode may become unwieldy to use and uncomfortable for the patient. Thus, to be self-limiting, the minimum bulk resistivity for an electrode of such thickness is about 4000 Ω·cm.

The preceding equations and discussion are representative of the bulk resistivity required for electrode 170 (FIG. 11) to be self-limiting. It may be appreciated, however, that the above analysis may be repeated to obtain the necessary self-limiting impedances for electrodes modeled using primarily capacitive or inductive components, or combinations of resistive, capacitive, and/or inductive components. Therefore, following is a discussion of the self-limiting requirements for the bulk impedance of electrode 170, whether such impedance arises from resistive, capacitive, and/or inductive components of impedance.

The self-limiting behavior of the electrosurgical electrode of the present invention results from the existence of sufficient return impedance to make an electrode site burn impossible when the area of contact between the patient and the electrosurgical return electrode is substantially reduced. As shown above, the combination of the maximum electrosurgical currents of 1000 mA coupled with the requirement that the current density be kept below 100 mA/cm$^2$ yields a minimum safe contact area of 10 cm$^2$.

In general, this requirement can be met with any number of electronic components hooked together in various configurations, including series and parallel combinations of capacitors, resistors, and even inductors, provided that the total impedance presented by the resulting circuit be about 75β or greater when the contact area is reduced to 10 cm$^2$.

Define the total impedance of the circuit between the return electrode of the electrosurgical generator and the patient as $Z_{TOT}$. This impedance is generated by the capacitive, resistive, and inductive properties of the materials inserted between the patient and the return electrode. We define the "bulk impedance" of the material η, a volume independent measure of the impedance of the material, that is frequency dependent, as:

$$\eta = \frac{(A)(Z_{TOT})}{t} \quad (16)$$

Here A is the area of the material and t is the thickness. This is analogous to the relationship between the volume dependent ohmic resistance R and the related volume independent characteristic of the resistive material called the "bulk resistivity" $\rho$ described earlier.

One manner to describe the self-limiting requirement is expressed in terms of $\eta$:

$$|Z_{TOT}| = \frac{t|\eta|}{A} > 75\beta \tag{17}$$

Or therefore $$|\eta| > \frac{(75\beta)A}{t} \tag{18}$$

For the previous case (minimum bulk resistivity specification) we used $A=A_{contact(min)}=10$ cm$^2$, (about 1.55 inch$^2$), $\beta=10$, and $t=t_{max}=1$ inch (about 2.5 cm), and a factor of 1.2 to account for edge effects to find that for a pure resistive electrosurgical electrode, $$|\eta| > 4000 \; \Omega \cdot cm \tag{19}$$

Therefore, in the purely resistive case, the bulk impedance ($\eta$) is identified as the bulk resistivity ($\rho$) of the conducting material in the electrode. The results in Equation 19, however, generalize to all materials and electrical components, including resistive, capacitive, and inductive components, and any combinations thereof. As long as the bulk impedance of the electrosurgical electrode is greater than 4000 $\Omega$·cm, the electrode will be self-limiting, regardless of whether the self-limiting behavior is due to a resistive, capacitive, inductive impedance, or any combination of these impedances.

As alternate illustrative examples, one might construct a self-limiting electrosurgical electrode using a conductive/resistive return plate coated with an insulating (dielectric) material or one might construct a patient gown out of dielectric material and use a metallic or resistive return electrode. The total effect of these devices would be to create a resistive impedance in series with a capacitive impedance.

For the above defined illustrative examples that model the return electrode in terms of resistive and capacitive impedances, the total impedance of the electrosurgical electrode is the sum of the resistive and the capacitive impedances, given by:

$$Z_{TOT} = R + \frac{1}{j\omega C} \tag{20}$$

In terms of the material bulk resistivity, dielectric constant, area, and thickness, the total impedance is:

$$Z_{TOT} = \frac{\rho t}{A} + \frac{t}{j\omega\kappa\varepsilon_0 A} \tag{21}$$

By multiplying both sides of the equation by the area A, and dividing by the thickness t, we can derive the bulk impedance $\eta$:

$$\eta = \rho + \frac{1}{j\omega\kappa\varepsilon_0} \tag{22}$$

The magnitude of the bulk impedance is:

$$|\eta| = \sqrt{\rho^2 + \frac{1}{(\omega\kappa\varepsilon_0)^2}} \tag{23}$$

If we require $$|\eta| > \frac{(75\beta)(1.2A)}{t} \tag{24}$$

Then $$\frac{A}{t} < \frac{|\eta|}{1.2(75\beta)} = \frac{\sqrt{\rho^2 + \frac{1}{(\omega\kappa\varepsilon_0)^2}}}{1.2(75\beta)} \tag{25}$$

As such, the edge effects reduce the bulk impedance of the electrode by about 10-20 percent, thereby causing a corresponding increase in the effective area of the self-limiting electrode by about 10-20 percent and reduce the possibility of unwanted electrosurgical burns.

Figure 14:
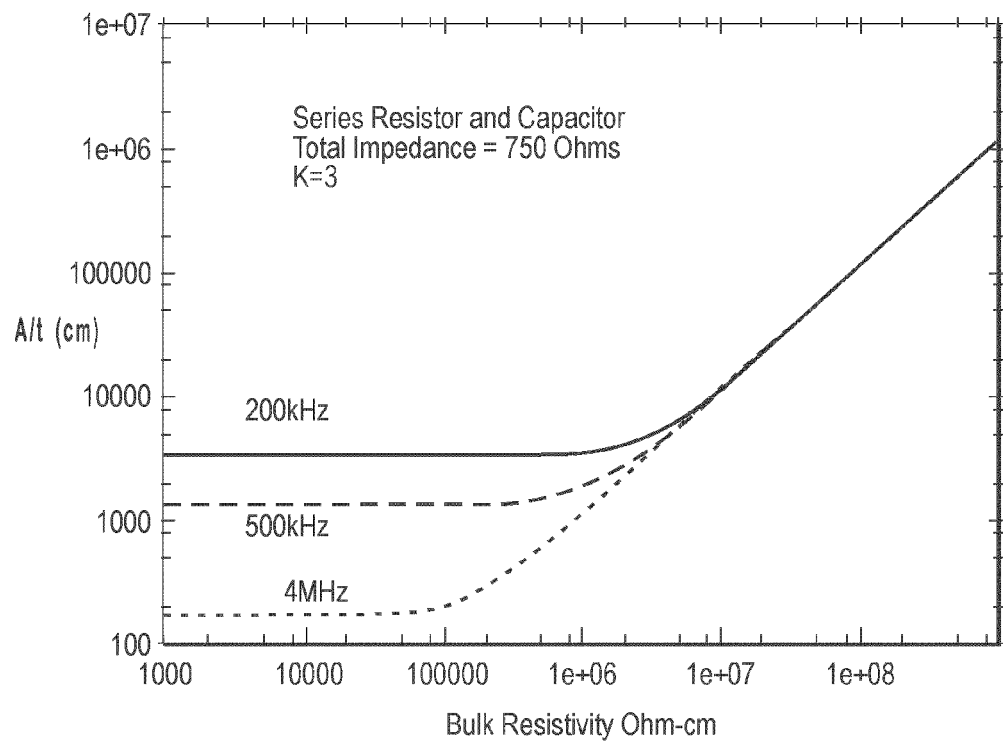
FIG. 14 is a graph showing bulk resistivity as a function of the area divided by the thickness of an electrosurgical return electrode in accordance with the present invention at various electrosurgical frequencies.

FIG. 14 plots A/t vs. bulk impedance $\eta$ for various electrosurgical frequencies. The y axis has the minimum ratio of A/t in order to have self-limiting behavior as a function of the bulk impedance. Note that we require bulk impedance always greater than 4000 $\Omega$·cm. On the right hand side of the plot, all of the curves merge into one. In this regime, the total impedance of the circuit is dominated by the resistive component and is, hence, independent of frequency. On the left hand side, the circuit impedance is dominated by the capacitive conduction of current. One requires area to thickness ratios of several hundred to about 10,000 in order to provide sufficient total impedance with the low ohmic resistance in this region.

The resulting lowest possible bulk impedance, therefore, is greater than that anticipated by U.S. Pat. No. 4,088,133, issued to Twentier; and, consequently, the self-limiting electrode according to the invention hereof appears to be neither taught nor suggested by known prior art. A product according to the invention hereof can be easily distinguished from previous art through a simple test of the bulk impedance, such as the bulk resistivity of the insulating material, independent of electrode area or electrode thickness.

Interrelationships of Geometries, Materials and Power Sources

As mentioned above, FIGS. 11-17 are set forth to define the geometries and characteristics of materials employed to obtain the foregoing self-limiting characteristics. Discussion will be made hereinafter to present illustrative information and an example related to an electrode that may be used for electrosurgical procedures utilizing capacitive conduction while still remaining self-limiting. Although discussion is made herein with respect to an electrosurgical electrode functioning under capacitive conduction, similar illustrative information and examples may be provided for resistive and inductive conduction, as known by one skilled in the art.

Figure 15:
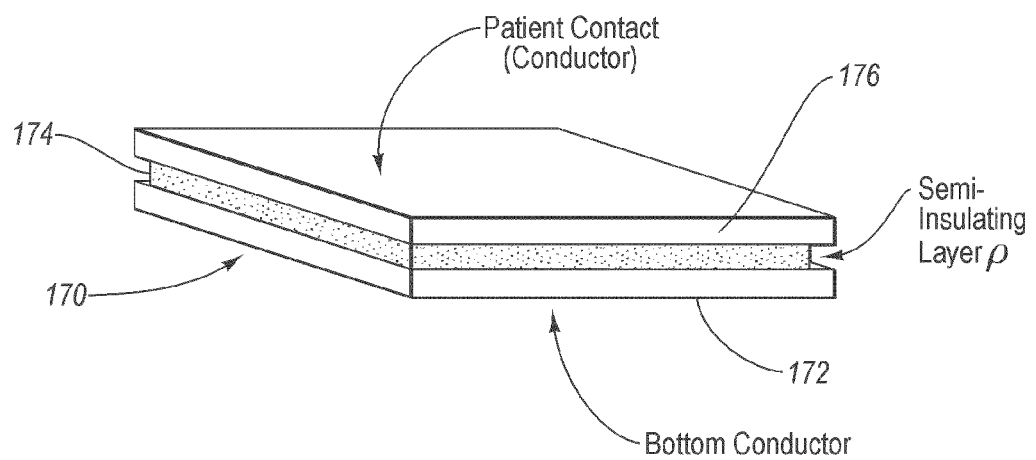
FIG. 15 is a perspective view illustrating, for the purpose of analysis, the circuit equivalent of a patient in operative association with the ohmic and capacitive regions of an electrode according to the invention.
Figure 16:
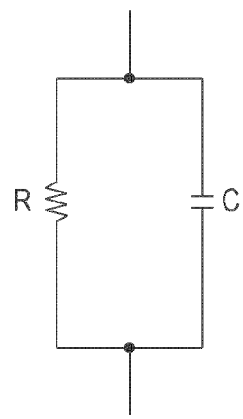
FIG. 16 is a simple electronic schematic circuit equivalent to FIG. 15.

FIG. 15 depicts electrosurgical electrode 170 consisting of conductive metal backing 172 and a semi-insulating layer 174 of material with bulk resistivity $\rho$, thickness t and area A. The electrode is in contact with another conducting layer 176 that represents a patient thereupon. The circuit can be modeled as a resistor R in parallel with a capacitor C as illustrated in FIG. 16. The resistance R is related to the bulk resistivity $\rho$, area A, and thickness t by the formula:

$$R = \frac{\rho t}{A} \tag{26}$$

The capacitance C is approximately related to the area A, thickness t, permittivity constant $\varepsilon_0 = 8.85 \times 10^{-12}$ F/m, and the dielectric constant of the material $\kappa$, as follows:

$$C = \frac{\kappa \varepsilon_0 A}{t} \quad (27)$$

The magnitude of the capacitor impedance is:

$$X_C = \frac{1}{\omega C} = \frac{t}{\omega \kappa \varepsilon_0 A} \quad (28)$$

The ratio Y of the current flow due to the capacitive path to the current flow due to the resistive path is:

$$Y = \frac{\frac{1}{X_C}}{\frac{1}{R}} = \frac{\frac{\omega \kappa \varepsilon_0 A}{t}}{\frac{A}{\rho t}} = \omega \kappa \varepsilon_0 \rho \quad (29)$$

The ratio Y is independent of the electrode area and thickness, depending only upon $\kappa$ and $\rho$. For principally capacitive coupling, $Y \gg 1$, whereas for principally resistive current, $Y \ll 1$, the boundary between the capacitive current and the resistive current is $Y=1$.

$$1 = 2\pi f \kappa \varepsilon_0 \rho \quad (30)$$

We can use this, along with the value of $\varepsilon_0$, to find the necessary values of $\rho$ for capacitive conduction, given nominal values of $\kappa$ and $\omega = 2\pi f$ where f is the electrosurgical generator frequency.

$$\rho = \frac{1}{2\pi f \kappa \varepsilon_0} \quad (31)$$

For most insulating materials, K ranges from 3 to 5. Commercially available electrosurgical generators presently have operating frequencies ranging from 200 kHz to 4 MHz. For $\kappa=5$ and f=4 MHz, it is preferred that $\rho \geq 1 \times 10^5$ $\Omega \cdot$cm for the electrosurgical electrode to return the majority of its current through capacitive coupling. For $\kappa=3$ and f=200 kHz, we require $\rho \geq 3 \times 10$ $\Omega \cdot$cm.

The percentage of total current derived through capacitive coupling is given by:

$$\text{pct} = \frac{\frac{1}{|X_C|^2}}{\frac{1}{|R|^2} + \frac{1}{|X_C|^2}} = \frac{|R|^2}{|R|^2 + |X_C|^2} = \frac{\left(\frac{\rho t}{A}\right)^2}{\frac{(\rho t)^2}{A} + \left(\frac{t}{A \varepsilon_0 \kappa \omega}\right)^2} \quad (32)$$

$$= \frac{\rho^2}{\rho^2 + \left(\frac{1}{\varepsilon_0 \kappa \omega}\right)^2} = \frac{(\varepsilon_0 \kappa \omega \rho)^2}{(\varepsilon_0 \kappa \omega \rho)^2 + 1}$$

Figure 17:
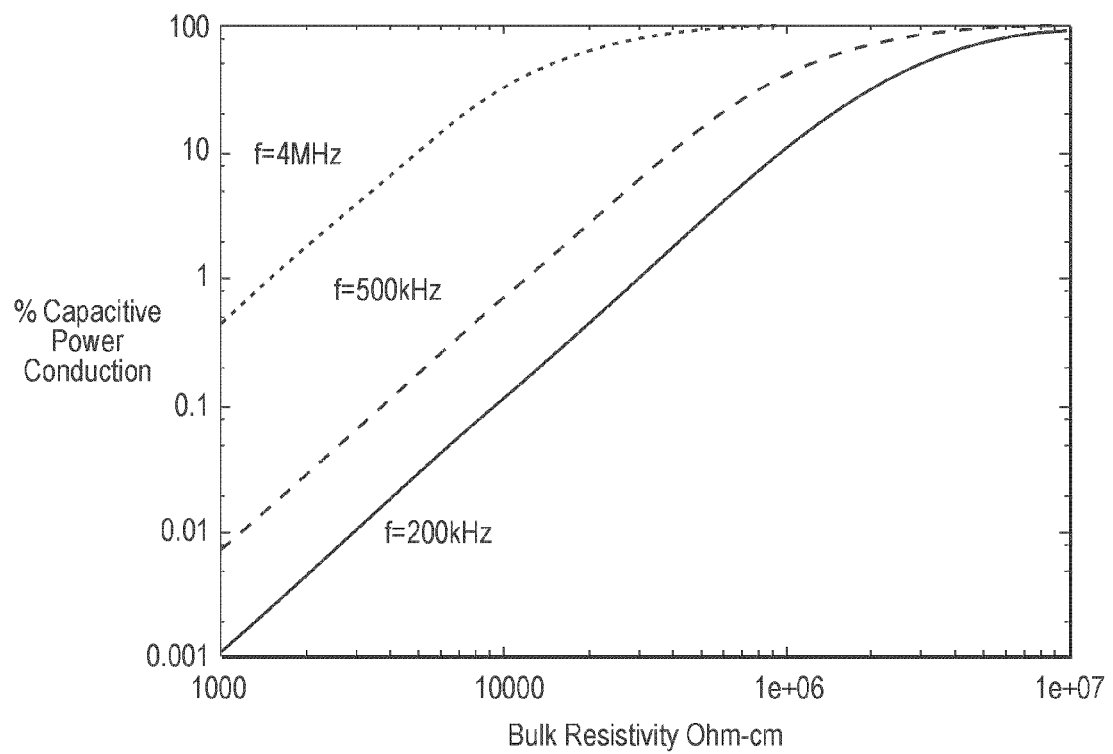
FIG. 17 is a graph depicting percent capacitive power conduction as a function of bulk resistivity of the resistive layer for different electrosurgical operating frequencies.

FIG. 17 illustrates the percentage (%) of capacitive coupling for various frequency electrosurgical generators. At the extreme (4 MHz), a minimum bulk impedance of $10^5$ $\Omega \cdot$cm is required for the majority of the current to be passed through capacitive coupling.

Electrode with Heating and Pressure Reducing Capabilities

Figure 18:
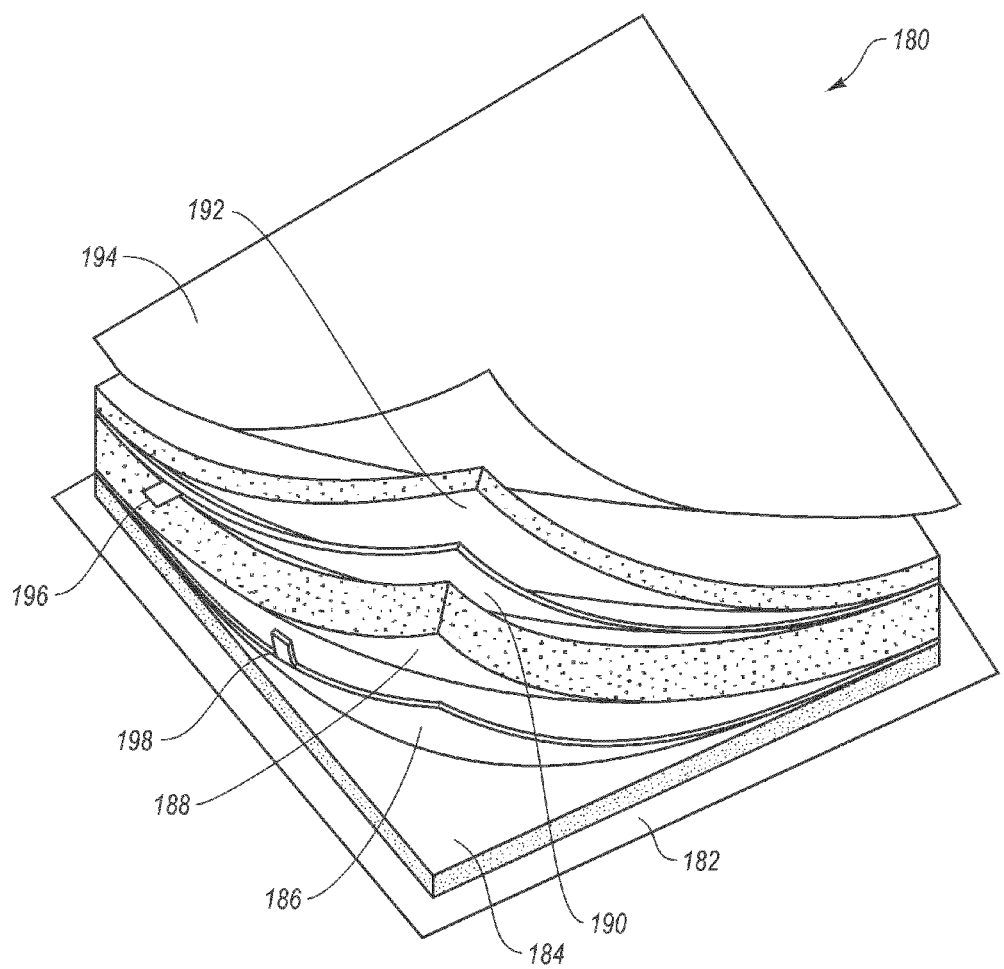
FIG. 18 illustrates a partially exploded view of an electrosurgical electrode according to one embodiment of the present invention.
Figure 19:
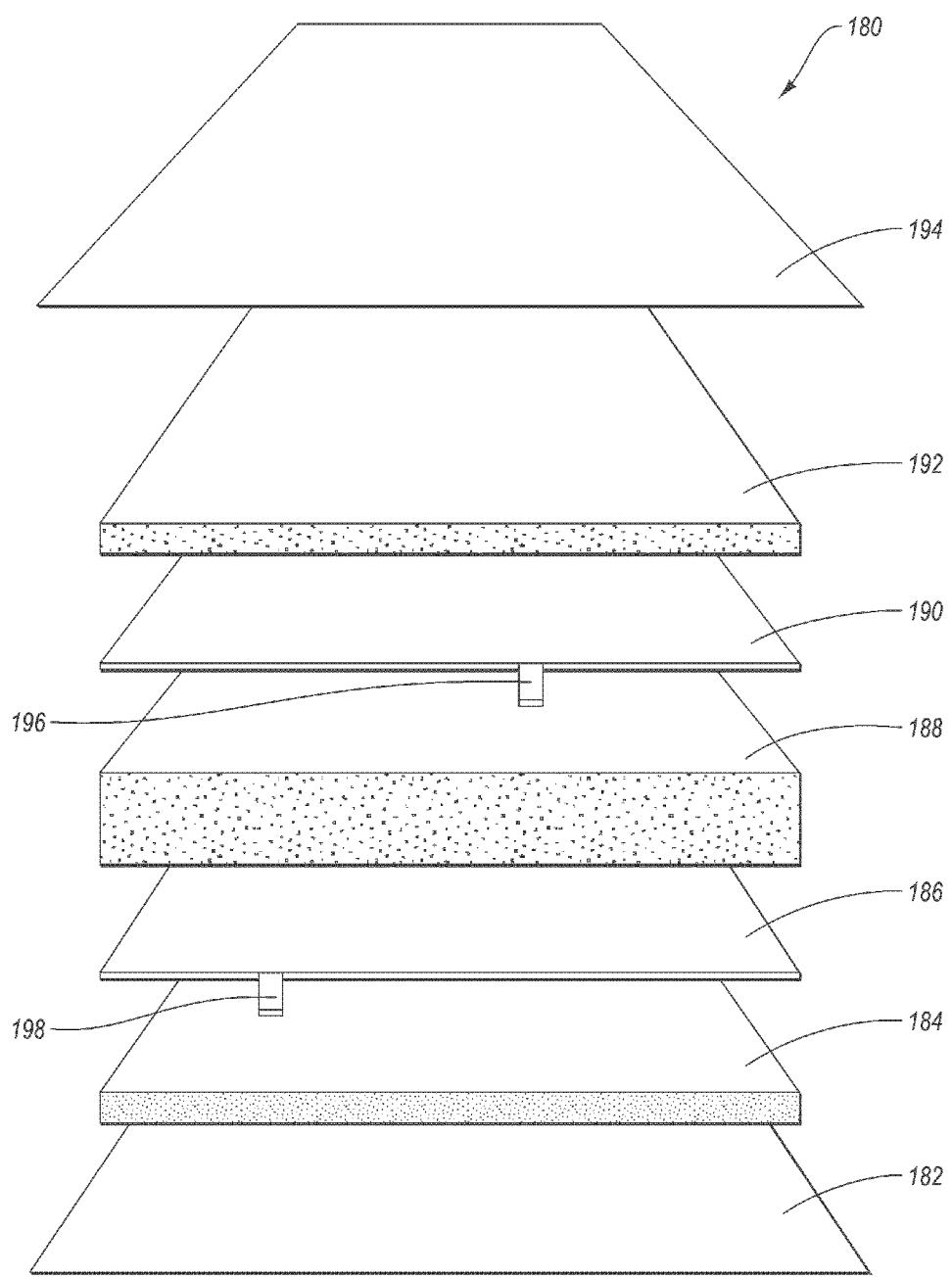
FIG. 19 illustrates an exploded view of some of the components of the electrosurgical electrode of FIG. 18 showing the construction of the electrosurgical electrode.

Referring now to FIGS. 18 and 19, an alternate embodiment of the present invention is depicted. The electrosurgical electrode illustrated in FIGS. 18 and 19 is self-limiting to prevent burning of a patient during an electrosurgical procedure, as described above. The illustrated electrosurgical electrode also includes a heating element that enables the electrosurgical electrode to warm a patient resting thereon. The illustrated electrosurgical electrode also includes one or more pads that help to reduce the possibility of decubitus ulcer or pressure sore creation that may arise during prolonged surgical procedures. By combining self-limiting characteristics with pressure sore reduction and heating properties, the electrosurgical electrode of the present invention provides the benefits of a self-limiting electrosurgical electrode as described herein while increasing the comfort level of a patient and protecting the patient from the creation of pressure sores.

An example of components implemented in one embodiment of the electrosurgical electrode is illustrated in FIGS. 18 and 19. These Figures illustrate the construction of the electrosurgical electrode including materials used to assemble the electrosurgical electrode. FIG. 18 illustrates a partially exploded view illustrating the flexible nature of electrosurgical electrode 180, which includes a first cover layer 182, a thermal insulation layer 184, a heating element 186, a first pressure sore pad 188, a conductive element or electrode 190, a second pressure sore pad 192, and a second cover layer 194. Electrosurgical electrode 180 further includes a conventional electrical connector 196 attached to electrode 190 to provide a conventional electrical return to the electrosurgical radio frequency energy source (not shown). Electrosurgical electrode 180 also includes an electrical connector 198 attached to heating element 186 to provide electrical power to heating element 186. While the example embodiment in FIG. 18 is illustrated as partially exploded, finished embodiments may be manufactured such that thermal insulation layer 184, heating element 186, first pressure sore pad 188, electrode 190, and second pressure sore pad 192 may be sealed between the first cover layer 182 and the second cover layer 194.

FIG. 19 illustrates a fully exploded view of electrosurgical electrode 180 so as to more clearly illustrate the individual components of electrosurgical electrode 180. As illustrated in FIG. 19, first and second cover layers 182 and 194 are generally planar sheets of material that are disposed on opposing sides of the internal components of electrosurgical electrode 180. During construction of electrosurgical electrode 180, first cover layer 182 is positioned as illustrated in FIG. 19. Next, thermal insulation layer 184 is positioned on top of first cover layer 182 with heating element 184 positioned on top of thermal insulation layer 184. First pressure sore pad 188 is then placed on top of heating element 186. Electrode 190 is then positioned on top of first pressure sore pad 188 and second pressure sore pad 192 is placed on top of electrode 190. Finally, second cover layer 194 is positioned on top of second pressure sore pad 192. With the various components of electrosurgical electrode 180 so positioned, the peripheral edges of first and second layers 182 and 194 can be joined, sealed, or otherwise closed.

As described herein, the various components of electrosurgical electrode 180 are flexible such that electrosurgical electrode 180 can generally conform to the shape of a patient's body when the patient is positioned on electrosurgical electrode 180. Additionally, the flexibility enables electrosurgical electrode 180 to be rolled or folded up when not in use, thereby making it easier to carry and store.

A more detailed description of the various components of electrosurgical electrode 180 will now be provided. While these components will be described with some specificity, including some exemplary materials that can be used for each component, it will be appreciated that the following descriptions are merely exemplary. The components of electrosurgical electrode 180 can be otherwise configured and/or arranged without departing from the scope of the present invention so long as electrosurgical electrode 180 provides the functionalities discussed herein, i.e., self-limiting, heating for patient, and pressure sore prevention.

In some embodiments, first and second cover layers 182 and 194 may be fabricated from various materials that are capable of being cleaned, sterilized, disinfected, and the like. First and second cover layers 182 and 194 may, therefore, be manufactured from various types of materials, including natural or synthetic products. For example, first and second cover layers 182 and 194 may comprise vinyl plastics, polyester, polyethylene, polyurethane, flexible sheet polymers, nylon, and the like. As noted above, with the various components of electrosurgical electrode 180 so positioned, the peripheral edges of first and second cover layers 182 and 194 can be joined, sealed, or otherwise closed. As illustrated in FIGS. 18 and 19, the first and second cover layers 182 and 194 extend slightly beyond the edges the internal components of electrosurgical electrode 180. This allows first and second cover layers 182 and 194 to be sealed, such as by using an adhesive, heat welding, or another appropriate method or combination of methods.

Electrode 190, in one configuration, is made of a conductive plastic, rubber or other flexible material which, when employed as a conductive element, will result in an effective DC resistance presented by each square centimeter of the working surface of electrosurgical electrode 180 (the surface that is in contact with or in close proximity to the patient) to be greater than about 8000 ohms or alternatively provide a bulk impedance of greater than 4000 Ω·cm. Various materials may be appropriate to give the required impedance. For example, silicone or butyl rubber have been found to be particularly attractive materials for electrode 190 as they are flexible, as well as readily washable, disinfectable, and sterilizable. Alternatively, in another embodiment, electrode 190 may be made of an inherently relatively high resistance flexible material altered to provide the requisite conductivity. One example of the latter is that of silicone rubber material in which there are impregnated conductive fibers, such as carbon black, quantities of gold, silver, nickel, copper, steel, iron, stainless steel, brass, aluminum, or other conductors.

In yet another alternate configuration, electrode 190 may be fabricated from a material that is substantially transparent to one or more wavelengths of electromagnetic radiation, such as but not limited to, microwave radiation, infra-red (IR) radiation, ultraviolet (UV) radiation, X-ray radiation, radio frequency (RF), and the like. This allows electrode 190 and electrosurgical electrode 180, when the other components of electrosurgical electrode 180 are transparent to one or more wavelengths of electromagnetic radiation, to be maintained in place during performance of certain medical procedures using particular wavelengths of electromagnetic radiation.

It may be appreciated by one skilled in the art that electrode 190 may have various other configurations so long as electrode 190 is capable of performing the functions of an electrode, i.e., being capable of passing current therethrough. For example, in another embodiment, electrode 190 includes a thin highly conductive lower stratum that facilitates connection of electrosurgical electrode 180 to an electrosurgical radio frequency energy source (not shown). In another alternate embodiment, electrode 190 is configured from multiple layers of conductors. In still yet another embodiment, electrode 190 includes an outer dielectric layer that substantially surrounds an interior-conducting layer, similar to the electrosurgical electrodes described previously.

Returning attention to FIGS. 18 and 19, the pressure sore prevention capabilities of electrosurgical electrode 180 will now be discussed. As noted above, the illustrated embodiment of electrosurgical electrode 180 includes first and second pressure sore pads 188 and 192. First and second pressure sore pads 188 and 192 are configured within electrosurgical electrode 180 so as to enable a patient to comfortably rest upon electrosurgical electrode 180 before, during, and/or after an electrosurgical procedure. As discussed in more detail below, first and second pressure sore pads 188 and 192 are adapted to conform to the contours of a patient's body, thereby increasing the contact area between the patient and electrosurgical electrode 180. The increased contact area resulting from first and second pressure sore pads 188 and 192 provides comprehensive and uniformly distributed support to the patient, thereby avoiding maladies such as pressure sores. In this manner, first and second pressure sore pads 188 and 192 support and distribute the weight and downward forces of a patient positioned upon electrosurgical electrode 180 throughout the entire return electrode to reduce the possibility of pressure sore creation. In addition to first and second pressure sore pads 188 and 192, in some exemplary embodiments, thermal insulation layer 184 may also provide comprehensive and uniformly distributed support to the patient to prevent the creation of pressure sores. Therefore, while the following discussion focuses on characteristics, features, and functions performed by first and second pressure sore pads 188 and 192, it will be appreciated that this discussion can be, in some embodiments, equally applicable to thermal insulation layer 184.

According to the illustrated embodiment, first and second pressure sore pads 188 and 192 are configured and arranged in a specific manner within electrosurgical electrode 180. In particular, second pressure sore pad 192 is placed on top of electrode 190 such that second pressure sore pad 192 is positioned between a patient and electrode 190 when a patient is positioned on electrosurgical electrode 180. Additionally, first pressure sore pad 188 is positioned between electrode 190 and heating element 186. Furthermore, as can be seen in the Figures, first pressure sore pad 188 is thicker than second pressure sore pad 192. While not required, these configurations and relative positions of first and second pressure sore pads 188 and 192 can contribute to the described functionality of electrosurgical electrode 180.

By way of non-limiting example, the relatively thin size of second pressure sore pad 192 can facilitate capacitive coupling between electrode 190 and a patient resting upon electrosurgical electrode 180. Through this capacitive coupling, current used during electrosurgery is passed from the patient to electrode 180. As will be understood by one of ordinary skill in the art in light of the disclosure herein, the capacitive coupling between the patient and electrode 190 can be directly related to the self-limiting characteristics of electrosurgical electrode 180. Thus, the relatively thin size of second pressure sore pad 192 contributes to good electrical coupling between the patient and electrode 190 so as to enable safe and effective electrosurgery.

In some embodiments, second pressure sore pad 192 may act as a dielectric layer to reduce the current that flows between the patient and electrode 190. Alternatively, second pressure sore pad 192 may take the form of a conducting material to aid with the transmission of current therethrough. Additionally, second pressure sore pad 192 may provide a thermal mass for the distribution of heat during an electrosurgical procedure. As discussed above, AAMI standards require that during an electrosurgical procedure the temperature rise of the patient's tissue should remain below six degrees Celsius (6° C.). The thermal mass provided by second pressure sore pad 192 can assist with the distribution of heat throughout the patient's body and substantially eliminate, in combination with the self-limiting characteristics of electrosurgical electrode 180, the potential for hot spots that may burn the patient. Consequently, the substances used for second pressure sore pad 192 may perform multiple functions during an electrosurgical procedure.

As noted above, first pressure sore pad 188 is relatively thick. The relatively thick size of first pressure sore pad 188 can contribute to the pressure sore prevention capabilities of electrosurgical electrode 180. First pressure sore pad 188 is thick enough and responsive enough to contour to a patient's body to uniformly support the patient and distribute the patient's weight to reduce the possibility of pressure sore creation. Additionally, the relatively thick size of first pressure sore pad 188 can act as an electrical insulation layer between electrode 190 and heating element 186. As will be appreciated by one of ordinary skill in the art, electrically insulating heating element 186 and electrode 190 can aid in the efficient performance of electrosurgical procedures.

In one aspect of this embodiment, first and second pressure sore pads 188 and 192, and optionally thermal insulation layer 184, are comprised of a "slow recovery" or "memory" foam, such as visco-elastic foam. This foam can be thermally conductive and selected to efficiently transfer heat from heating element 186 to a patient positioned on electrosurgical electrode 180. This foam also demonstrates favorable compression characteristics, thereby decreasing the point forces applied to those parts of the patient where bony prominences are located. In this manner, first and second pressure sore pads 188 and 192 reduce the pressure exerted upon the patient and thereby limit the generation of pressure sores.

According to the present embodiment in which a foam material is used, the total thicknesses of first and second pressure sore pads 188 and 192 can range anywhere from about 0.22 inches to about 3.5 inches. For instance, when first pressure sore pad 188 is formed of visco-elastic foam, first pressure sore pad 188 may have a thickness between about 0.20 inches and about 3.0 inches, and more preferably between about 0.25 inches and about 2.0 inches. Forming first pressure sore pad 188 within these ranges can provide the functionality described above. For instance, forming first pressure sore pad 188 of a foam material with such a thickness can allow first pressure sore pad 188 to electrically insulate electrode 190 and heating element 186 while also providing substantially uniform support to the patient and distribution of the patient's weight to reduce the possibility of pressure sore creation.

Similarly, when second pressure sore pad 192 is formed of visco-elastic foam, second pressure sore pad 192 may have a thickness between about 0.02 inches and about 0.5 inches, and more preferably between about 0.05 inches and about 0.3 inches. Forming second pressure sore pad 192 within these ranges can provide the functionality described above. For instance, forming second pressure sore pad 192 of a foam material with such a thickness can allow second pressure sore pad 192 to facilitate capacitive coupling between electrode 190 and the patient resting on electrosurgical electrode 180, thereby affecting the self-limiting characteristics of electrosurgical electrode 180 and, thus, enabling safe and effective electrosurgery. Second pressure sore pad 196 can also provide substantially uniform support to the patient and distribution of the patient's weight to reduce the possibility of pressure sore creation.

In an alternative embodiment, each of first and second pressure sore pads 188 and 192, and optionally thermal insulation layer 184, can be formed with one or more chambers filled with a material that provides the pressure reducing characteristics discussed herein. More specifically, since a defined volume of material is retained within the chambers of first and second pressure sore pads 188 and 192, and optionally thermal insulation layer 184, when an individual rests upon electrosurgical electrode 180, the material distributes the downward force of the patient throughout the material, thereby decreasing the point forces applied to those parts of the patients anatomy where bony prominences are located. In this manner, first and second pressure sore pads 188 and 192, and optionally thermal insulation layer 184, reduce the pressure exerted upon the patient and thereby limit the generation of pressure sores.

As with the embodiment in which first and second pressure sore pads 188 and 192 are formed of a foam material, the material filling the chambers of first and second pressure sore pads 188 and 192 in the present embodiment may act as a dielectric layer to reduce the current that flows through first or second pressure sore pads 188 and 192. Alternatively, the material may take the form of a conducting material to aid with the transmission of current therethrough. Additionally, the fill material may provide a thermal mass for the distribution of heat during an electrosurgical procedure to assist with the distribution of heat throughout the patient's body and substantially eliminate, in combination with the self-limiting characteristics of electrosurgical electrode 180, the potential for hot spots that may burn the patient. Consequently, the substances used for the fill material may perform multiple functions during an electrosurgical procedure.

In general, the material used to fill the chambers of first and second pressure sore pads 188 and 192, and optionally thermal insulation layer 184, may take the form of one or more solids, liquids, gases, or combinations thereof depending on the pressure reducing, dielectric, and/or conducting properties needed for electrosurgical electrode 180. For example, in one illustrative embodiment, the fill material is an elastomeric gel having a low durometer level, such as sorbethane. In addition to sorbethane, various other elastomeric gels may used, such as but not limited to those based upon the polymer chemistry of urethanes, silicones, hydrophilic elastomers or hydrogels, vinyls, vinyl alcohols, or other similar materials and technologies. Additionally, the fill material may take the form of water, saline, water based materials, conductive oils, and the like.

Furthermore, the variety of materials from which first and second pressure sore pads 188 and 192, and optionally thermal insulation layer 184, can be formed can have a variety of characteristics. For instance, visco-elastic foams can be formed with a wide range of densities which can affect the comfort level of the patient. Additionally, the materials can be adapted to respond to various environmental conditions. In some embodiments, for example, visco-elastic foams can be adapted to become softer has heat is applied. Thus, when a patient is resting on electrosurgical electrode 180, the patient's body heat and/or the heat from heating element 186 can cause first and second pressure sore pads 188 and 192, and optionally thermal insulation layer 184, to soften, thereby further conforming to the contours of the patient's body.

While the present embodiment has been shown and described with first pressure sore pad 188 being thicker than second pressure sore pad 192, it will be appreciated that the illustrated configuration of the two pressure sore pads is not necessary to the present invention. For instance, first and second pressure sore pads 188 and 192 may have substantially the same thickness, or second pressure sore pad 192 may be thicker than first pressure sore pad 188. Likewise, the relative thickness of thermal insulation layer 184 compared to first and second pressure sore pads 188 and 192 is not intended to limit the scope of the present invention. Additionally, first and second pressure sore pads 188 and 192 and thermal insulation layer 184 may be formed of different materials to provide desired functionality. For instance, first pressure sore pad 188 may be formed with a chamber filled with a gel while the second sore pad 192 may be formed of viscoelastic foam, or vice versa.

The selection of the materials and the specific configurations for each of first and second pressure sore pads 188 and 192 and thermal insulation layer 184 can be made so that first and second pressure sore pads 188 and 192 and thermal insulation layer 184 can provide the functionality described herein (i.e., capacitive coupling between patient and electrode 190, electrical insulation between heating element 186 and electrode 190, pressure sore prevention, and thermal insulation between heating element 186 and the operating table). Likewise, first pressure sore pad 188 or second pressure sore pad 192 may be removed. For example, if heating element 186 is not formed of a conductive material, first pressure sore pad 188 may be removed without capacitively decoupling the patient and electrode 190.

Furthermore, while the various internal elements of electrosurgical electrode 180 are illustrated and have been described as being separate and distinct layers, it will be appreciated that the various internal layers of electrosurgical electrode 180 can be integrally formed or can become integrated with one another during the formation of electrosurgical electrode 180. For instance, thermal insulation layer 184 and first and second pressure sore pads 188 and 192 may be formed of a material or through a process such that these layers are integrally formed or are joined together to make an integral unit. For instance, thermal insulation layer 184 and first and second pressure sore pads 188 and 192 may each be formed of a foam material that is arranged as shown in FIGS. 18 and 19. Alternatively, for example, when thermal insulation layer 184 and first and second pressure sore pads 188 and 192 are formed of a gel, these layers may be individually poured or molded to form each layer, after which the various layers become or are joined together. More specifically, thermal insulation layer 184 may be formed of a gel material which is poured or molded to form thermal insulation layer 184. Heating element 186 may then be placed on thermal insulation layer 184. A gel may then be poured or molded to form first pressure sore pad 188 on heating element 186. Electrode 190 may then be placed on first pressure sore pad 188, and a gel may be poured or molded to form second pressure sore pad 192 on electrode 190. This process and/or the materials used may cause these various layers to become joined or integrated together such that the layers are no longer separable.

Attention is now directed to heating element 186. Heating element 186 is adapted to produce heat for warming a patient positioned on electrosurgical electrode 180. As noted elsewhere herein, there are numerous advantages to incorporating heating element 186 within electrosurgical electrode 180. Some of the advantages include the convenience of using one device to both warm a patient and to provide the functionality of a return electrode. Another advantage of incorporating heating element 186 into electrosurgical electrode 180 over conventional warming devices that warm the patient from the topside, such as pre-warmed blankets, is that the heat is more efficiently applied to the patient's body through the comprehensive support provided beneath the patient. Pre-warmed blankets placed over the patient waste thermal energy that rises upward off the blankets away from the patient. In contrast, electrosurgical electrode 180 and heating element 186 are positioned beneath the patient so that thermal energy rising from heating element 186 will naturally be absorbed by the patient and not wasted. A further advantage of the present invention is that it affords hospital personnel complete access to the patient without compromising patient warmth.

Heating element 186 may take any one of a number of forms. In one implementation, heating element 186 may comprise a system that produces heat for warming a patient. Such a system may include a heated material that is circulated through one or more conduits within electrosurgical electrode 180. An example of such a heating system is described in U.S. Pat. No. 6,544,258, issued to Fleenor et al., and entitled "Pressure Sore Pad Having Self-Limiting Electrosurgical Return Electrode Properties and Optional Heating/Cooling Capabilities," the disclosure of which is incorporated by this reference in its entirety.

In another implementation, heating element 186 comprises a carrier material impregnated with carbon such that the carrier material becomes an electrically conductive material. In some embodiments, the carrier material can be an elastomeric polymer. On the conductive material are one or more conductive rails or poles which facilitate electrical connection between the conductive material and an electrical power source. In such a configuration, electrical current can be passed from the power source through the conductive rail and into the conductive material. The carbon particles dispersed throughout the carrier material generate heat when the electrical current is passed therethrough. The polymer carrier material can act as a heat spreader to evenly spread the generated heat over the surface of the conductive material. The heat generated can be transferred from the heating element, through the other components of electrosurgical electrode 180, and to a patient positioned on electrosurgical electrode 180. Examples of such carbon impregnated materials are available from Inditherm PLC located in the United Kingdom, and are described in U.S. Pat. No. 6,814,889, to O'Grady et al., and entitled "Conductive Materials," the disclosure of which is incorporated by this reference in its entirety.

Other embodiments of heating element 186 include heated fabrics that are knitted using conductive fibers and either merino wool, fire retardant polyester, or aramids to deliver the desired heating properties. Because these fabrics are knitted, they are stretchable and robust. For example, these fabrics can still safely provide evenly distributed heat when they have been cut, torn, or have holes in them. Additionally, these heated fabrics can withstand rigorous pulling, rubbing and stretching without damage. When knitted with merino wool, these heated fabrics have the additional safety of being self-extinguishing. Furthermore, these fabrics are readily washable and sterilizable. Examples of such heated fabrics are available from Wera located in New Zealand, and are described in PCT Publication No. 2008/013459, to Wichman, and entitled "Textile Articles Incorporating an Electrical Heating Element(s)," the disclosure of which is incorporated by this reference in its entirety. Other exemplary heated fabrics that may be suitable for use as heating element 186 include the heated fabrics available from Malden Mills Industries, Inc. located in Lawrence, Mass. and described in one or more of U.S. Pat. Nos. 6,160,246; 6,723,967; 6,852,956; 6,875,963; 6,963,055; and 7,038,177.

In still yet other embodiments, heating element 186 may include a heat generating strip and a heat spreading element. The heat generating strip may be, for example, an electrothermal coupling material or resistive element. In some embodiments, the heat generating strip may be a copper, copper alloy or other conductor. The conductor may convert electrical energy to heat energy, and transfer the heat energy to the surrounding environment. Alternatively, the heat generating element may comprise another conductor, such as semiconductors, ceramic conductors, other composite conductors, etc., capable of converting electrical energy to heat energy. The heat generating strip may include one or more layers for electrical insulation and temperature regulation. The heat spreading element may be a thermally conducting material that is adapted to conduct heat away from the heat generating strip and evenly spread the heat over the surface of the heat spreading material. Examples of some heat spreading materials include highly conductive metals such as copper and aluminum (or alloys, thereof), or a material such as graphite.

Notably, the exemplary heating elements described herein are not intended to be a complete list of heating elements that can be incorporated into electrosurgical electrode 180. Other heating elements or systems that may be suitable for use as heating element 186 may also include polymers coated with conductive ink or flexible heating strips formed of tungsten, for example. Thus, other heating elements may be used in addition to or as alternatives to the heating elements described herein.

Furthermore, any heating element incorporated into electrosurgical electrode 180 can also include control circuitry or other means for regulating the amount of heat generated by heating element 186. The control circuitry can provide electrical power to heating element 186 via electrical connector 198. The control circuitry can, optionally, monitor the performance of heating element 186 to ensure proper functionality. Heating element 186 and any associated control circuitry can be operatively independent. That is, heating element 186 and any associated control circuitry can be controlled without affecting or being affected by the performance of other components of electrosurgical electrode 180. In this manner, heating element 186 can be employed to provide heat to a patient resting on electrosurgical electrode 180 even if electrosurgical electrode 180 is not being used as a return path for electrosurgical current. Heating element 186 may also include additional safety features. For example, heating element 186 may be formed of or include flame retardant materials and/or coatings, circuit breakers, fuses, semiconductor based overcurrent protection, ground fault protection, arc fault protection, and the like.

Various factors can be considered when selecting a heating element for inclusion in electrosurgical electrode 180. For instance, selection of a flexible heating element can contribute to both the performance and the convenience of using and storing electrosurgical electrode 180. More specifically, a flexible heating element allows electrosurgical electrode 180 to more readily contour to the shape of the patient's body, thus leading to better capacitive coupling between electrode 190 and the patient as well as helping prevent the creation of pressure sores.

As with most components of electrosurgical electrode 180, heating element 186 should be durable and long lasting. Large return electrodes, heating pads, pressure sore prevention pads are each used repeatedly and are often folded or rolled up for storage between uses. Thus, a heating element incorporated into electrosurgical electrode 180 should be able to withstand repeated use, folding, and rolling. This is particularly important with the present invention in that heating element 186 is incorporated into electrosurgical electrode 180, and replacing heating element 186 may be difficult or at least inconvenient. Therefore, it is desirable for heating element 186 to be flexible and durable to contribute to a relatively long life for electrosurgical electrode 180.

In that electrosurgical electrode 180 can be configured to be used before, during, and after an electrosurgical procedure, is can be desirable to form electrosurgical electrode 180 of materials that do not interfere with other medical procedures. For instance, as with electrode 190 discussed above, heating element 186 may be formed from materials that are substantially transparent to one or more wavelengths of electromagnetic radiation, such as but not limited to, microwave radiation, infra-red (IR) radiation, ultraviolet (UV) radiation, X-ray radiation, radio frequency (RF), and the like. This allows heating element 186 and electrosurgical electrode 180, when the other components of electrosurgical electrode 180 are transparent to one or more wavelengths of electromagnetic radiation, to be maintained in place during performance of certain medical procedures using particular wavelengths of electromagnetic radiation.

Other considerations in selecting the components for heating element 186 include the accuracy, responsiveness, and uniformity of the components as they relate to the temperature. In some heating applications, particularly industrial applications, temperature accuracy, responsiveness, and uniformity are of less concern. However, in the medical field where heat is applied to a patient, temperature accuracy, responsiveness, and uniformity are of high importance. Therefore, the components selected for heating element 186 should be highly responsive to temperature controls and should produce temperatures that are within tightly controlled tolerances. Additionally, the heating element components should be able to produce desired temperatures (e.g., 32-40° C.) within a reasonable time, preferable less than one hour. Furthermore, for safety reasons as well as comfort of the patient, the heating element should produce substantially uniform temperatures across the working surface of the electrosurgical electrode. Substantially uniform temperatures ensure that there are not hot spots that could be uncomfortable or cause injury to a patient, or cold spots that could also be uncomfortable to a patient.

With attention once again to FIGS. 18 and 19, thermal insulating layer 184 will now be discussed in greater detail. Thermal insulation layer 184 may be used to reflect or direct heat or to prevent heat from exiting electrosurgical electrode 180 in an undesired direction. For example, it may be desirable to have all or most of the heat generated by heating element 186 to be directed towards a patient resting upon electrosurgical electrode 180 and away from an operating room table upon which electrosurgical electrode 180 is positioned. In the embodiment illustrated in FIGS. 18 and 19, for example, electrosurgical electrode 180 may be positioned on a operating room table with first cover layer 182 being in contact with the operating room table and second cover layer 184 positioned such that a patient may lie thereon. In this configuration, it may be desirable to direct heat towards second cover layer 194 while directing heat away from first cover layer 182. Thermal insulation layer 184 may be used to accomplish this task. In particular, positioning thermal insulation layer 184 between heating element 186 and first cover layer 182 directs heat generated by heating element 186 away from first cover layer 182 and towards second cover layer 184.

Thermal insulation layer 184 may include a sheet of polystyrene, cotton batting, GORE-TEX®, gel, fiberglass, foam rubber, etc. In certain embodiments, thermal insulation layer 184 may be integrated with either first cover layer 182 or heating element 186. For example, first cover layer 182 may include an insulation fill or batting positioned between two films of nylon. In light of the disclosure herein, and as noted above, it will be appreciated that thermal insulation layer 184 can also be formed of a material that provides pressure sore prevention capabilities similar to first and second pressure sore pads 188 and 192.

In some embodiments of the present invention, thermal insulation layer 184 may be omitted. More particularly, when a surgical table or chair provides a thermal barrier that will direct heat from heating element 186 towards second cover layer 194, thermal insulation layer 184 may not be needed to perform this function. In such a case, an electrosurgical electrode according to the present invention could be formed without a thermal insulation layer.

The materials forming electrosurgical electrode 180, including electrode 190 and second pressure sore pad 192, control the passage of current from the patient to electrode 190. As such, in one embodiment, second pressure sore pad 192 is insulative, while in an alternate configuration second pressure sore pad 192 may be conductive and aid in the passage of current from the patient to electrode 90. So long as the total impedance of electrosurgical electrode 180 is within the limits defined herein, i.e., each square centimeter of the working surface being greater than 8000 ohms or bulk impedance greater than 4000 $\Omega \cdot cm$, the various elements of electrosurgical electrode 180, i.e., electrode 190 and second pressure sore pad 192, may provide one or more resistive, inductive, and/or capacitive inductance components to the bulk impedance. In this manner electrosurgical electrode 180 is self-limiting, while providing heating capabilities and pressure reducing characteristics.

It may be appreciated by one skilled in the art that various other configurations of electrosurgical electrode 180 are applicable. For example, in another configuration, electrosurgical electrode 180 may be built into an operating room table such that the operating table has patient warming and pressure sore reduction capabilities in addition to self-limiting capabilities. In another configuration, electrosurgical electrode 180 need not be used for electrosurgical procedures but may be used as only a heating blanket/pad or pressure sore pad. By so doing, creation of electrosurgical electrode 180 and the other related electrodes described herein reduce the need for a medical facility to purchase and store multiple different heating blankets/pads, pressure sore pads, and electrosurgical return electrodes. Additionally, the electrosurgical electrode may be used multiple times since it is sterilizable, cleanable, washable, and disinfectable. In another configuration of the present invention, electrosurgical electrode 180 may be used with other heating blankets and pressure sore devices, even though such other devices have a number of disadvantages as described previously.

By creating a combined heating blanket, pressure sore pad, and electrosurgical return electrode, the bulk impedance may be defined, thereby eliminating the possibility of reduced efficacy of an electrosurgical return electrode when such an electrosurgical return electrode is combined with other heating blankets or pressure sore devices with unknown bulk impedances.

It will now be evident that there has been described herein an improved electrosurgical return electrode characterized by being generally electrode-shaped and including a conformable pad. The improved electrosurgical return electrode evidencing the features of being self-limiting while being reusable, readily cleanable and obviating the necessity for use of conducting gels or supplementary circuit monitoring equipment, while providing a conformable platform upon which a patient may rest that reduces the incidence of pressure sores. Further, the improved electrosurgical return electrode provides the features of heating to thereby warm a patient during a surgical procedure or during recovery of the patient. Similarly, the electrosurgical return electrodes of the present invention can be utilized during any surgical procedure, during recovery of the patient from the surgical procedure, while the patient is hospitalized, or the like.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An electrosurgical electrode comprising:
   one or more pads configured to substantially prevent the creation of one or more pressure sores on a patient resting upon said electrosurgical electrode, said one or more pads comprising at least one pad having a first side and an opposing second side;
   a conductive element configured to conduct electrical current, said conductive element being positioned adjacent said first side of said at least one pad; and
   a heating element comprising a heat generating element and a heat spreading element, said heat generating element being adapted to generate heat for warming a patient resting upon said electrosurgical electrode when an electrical current is passed through the heat generating element, the heat spreading element being configured to conduct the heat away from the heat generating element and evenly distribute the heat uniformly over a surface area of the electrosurgical electrode, said heat generating element being disposed within and coplanar with said heat spreading element, the heating element being positioned adjacent said opposing second side of said at least one pad such that said heating element and said conductive element are spaced apart from one another by said at least one pad,
   wherein, said conductive element and said one or more pads have an effective bulk impedance equal to or greater than about 4,000 $\Omega \cdot m$.

2. The electrosurgical electrode according to claim 1, further comprising a thermal insulation layer positioned adjacent said heating element on a side of said heating element opposite to said at least one pad, said thermal insulation layer being adapted to direct the heat generated by said heating element towards said at least one pad.

3. The electrosurgical electrode according to claim 1, wherein the electrosurgical electrode comprises a top surface configured to have a patient rest thereon, wherein one of said one or more pads is positioned on top of said conductive element such that said pad is positioned between said conductive element and said top surface.

4. The electrosurgical electrode according to claim 1, wherein said one or more pads comprise a material selected from the group consisting of a visco-elastic material, a gel, water, saline, a water based material, a conductive oil, or combinations thereof.

5. The electrosurgical electrode according to claim 1, wherein said heating element is positioned near a bottom surface of said electrosurgical electrode.

6. The electrosurgical electrode according to claim 1, wherein said heating element comprises a fabric formed of conductive fibers.

7. The electrosurgical electrode according to claim 1, wherein said conductive element comprises normally insulating material impregnated with electrically conducting fibers to render said electrosurgical electrode to have an effective bulk impedance equal to or greater than about 4,000 $\Omega$·cm.

8. The electrosurgical electrode according to claim 1, wherein said effective bulk impedance of said conductive element and said one or more pads comprises electrical components selected from the group consisting of resistance, capacitive, inductive, or combinations thereof.

9. The electrosurgical electrode according to claim 1, wherein said conductive element comprises:
an electrode, said electrode comprising:
a first layer of predetermined limited electrical conductivity; and
a second layer of dielectric material having a predetermined capacitive reactance, said second layer contacting and overlying said first layer.

10. An electrosurgical electrode for warming a patient resting upon the electrosurgical electrode and preventing the creation of pressure sores on the patient, the electrosurgical electrode comprising:
a conductive element configured to conduct electrical current, the conductive element having a first surface and an opposing second surface;
an electrical heating element comprising a heat generating element and heat spreading element, the heat generating element being adapted to convert electrical energy to heat energy and the heat spreading element being generally planar and substantially uniform, heat spreading element being adapted to conduct the heat energy away from the heat generating element and evenly distribute the heat energy uniformly so as to warm a patient resting upon said electrosurgical electrode, the electrical heating element having a first surface and an opposing second surface and said heat generating element being disposed within and coplanar with said heat spreading element; and
first and second pads adapted to substantially prevent the creation of one or more pressure sores on a patient resting upon said electrosurgical electrode, said first pad being positioned between said conductive element and said electrical heating element such that said first surface of said conductive element is positioned adjacent a first side of said first pad and said first surface of said electrical heating element is positioned adjacent an opposing second side of said first pad, and said second pad being positioned adjacent said opposing second surface of said conductive element such that said second pad is positioned between said conductive element and a patient resting upon said electrosurgical electrode,
wherein, said electrosurgical electrode has a collective bulk resistance equal to or greater than about 4,000 $\Omega$·cm.

11. The electrosurgical electrode according to claim 10, wherein said first pad is substantially thicker than said second pad.

12. The electrosurgical electrode according to claim 10, wherein at least one of said first and second pads is formed of a visco-elastic material.

13. The electrosurgical electrode according to claim 10, wherein at least one of said first and second pads is formed of a gel.

14. The electrosurgical electrode according to claim 10, wherein at least one of said first and second pads is formed of water, saline, a water based material, a conductive oil, or a combination thereof.

15. The electrosurgical electrode according to claim 10, wherein said first and second pads are thermally conductive.

16. The electrosurgical electrode according to claim 10, wherein said conductive element comprises electrically conducting material having an effective bulk resistivity equal to or greater than about 4,000 $\Omega$·cm.

17. The electrosurgical electrode according to claim 10, wherein said first pad is between about 0.20" and about 3.0" thick.

18. The electrosurgical electrode according to claim 10, wherein said second pad is between about 0.05" and about 0.50" thick.

19. An electrosurgical electrode configured to be disposed beneath a patient during electrosurgery to provide a return path for an electrosurgical current used in electrosurgery, the electrosurgical electrode being self-limiting such that the electrosurgical current is limited to safe thresholds so as to prevent an undesirable patient burn at the contact area between the patient and the electrode in the event of an accidental reduction in the contact area below a threshold level, the electrosurgical electrode comprising:
a first cover layer and a second cover layer associated with one another to form an envelope with an interior portion;
a heating element comprising a heat generating element and a heat spreading element, the heating element being disposed within said interior portion, said heat generating element being adapted to generate heat, said heat spreading element being generally planar and substantially uniform, said heat spreading element being adapted to conduct the heat energy away from the heat generating element and evenly distribute the heat energy uniformly for warming the patient resting upon said electrosurgical electrode, said heat generating element being disposed within and coplanar with said heat spreading element;
a conductive element disposed within said interior portion of said envelope and above said heating element, said conductive element being configured to conduct electrical current;
first and second pads disposed within said interior portion, said first pad being positioned between said heating element and said conductive element, said second pad being positioned between said conductive element and said second cover layer, said first and second pads being adapted to substantially prevent the creation of one or more pressure sores on the patient resting on said electrosurgical electrode; and
a thermal insulation layer disposed between said first cover layer and said heating element such that said thermal insulation layer directs heat away from said first cover layer and toward said heating element and said conductive element,
wherein, the effective bulk impedance of said second pad and said conductive element is equal to or greater than about 4,000 $\Omega$·cm.

20. The electrosurgical electrode according to claim 19, wherein said first and second pads are adapted to transfer the heat generated by said heating element to the patient resting on said electrosurgical electrode.

21. The electrosurgical electrode according to claim 19, wherein said heating element comprises electrically conductive fibers and at least one of wool, polyester, or an aramid.

22. The electrosurgical electrode according to claim 19, wherein said heating element comprises a carbon impregnated polymer.

23. The electrosurgical electrode according to claim 19, wherein said thermal insulation layer directs heat toward said second cover layer.

24. The electrosurgical electrode according to claim 19, wherein said thermal insulation layer is adapted to substantially prevent the creation of one or more pressure sores on the patient resting on said electrosurgical electrode.

25. The electrosurgical electrode according to claim 19, wherein said first pad is between about 0.20" and about 3.0" thick and said second pad is between about 0.05" and about 0.50" thick.

\* \* \* \* \*